United States Patent
Blumenfeld et al.

(10) Patent No.: US 6,551,792 B1
(45) Date of Patent: Apr. 22, 2003

(54) NUCLEOTIDE SEQUENCE WHICH ENCODES A FLAVIN MONOOXYGENASE, THE CORRESPONDING PROTEIN AND THEIR USES IN THE SPHERES OF DIAGNOSIS AND THERAPY

(75) Inventors: Marta Blumenfeld, Paris (FR); Ilia Tchoumakov, Vaux-le-Penil (FR); Henri-Jean Garchon, Paris (FR); Jean-Francois Bach, Paris (FR)

(73) Assignees: Genset, S.A. (FR); Institute National de la Sante et de la Recherche Medicale (FR)

( * ) Notice: Subject to any disclaimer, the term of this patent is extended or adjusted under 35 U.S.C. 154(b) by 0 days.

(21) Appl. No.: 09/326,480

(22) Filed: Jun. 4, 1999

Related U.S. Application Data

(63) Continuation of application No. PCT/FR97/02226.

(30) Foreign Application Priority Data

Dec. 6, 1996 (FR) ............................................. 96 15032

(51) Int. Cl.$^7$ ............................ C12Q 1/26; C12N 9/02; C12N 9/04; G01N 33/566; C12P 21/06

(52) U.S. Cl. ........................ 435/25; 435/189; 435/190; 435/69.1; 435/325; 435/252.3; 435/320.1; 530/350; 536/23.2; 436/501

(58) Field of Search ................................. 435/189, 190, 435/25, 69.1, 325, 252.3, 320.1; 530/350; 436/501; 536/23.2

(56) References Cited

U.S. PATENT DOCUMENTS 5,843,869 A * 12/1998 Schulz ....................... 504/348

FOREIGN PATENT DOCUMENTS

EP 0 712 932 A2 11/1995

OTHER PUBLICATIONS

Lawson et al., J. Biol. Chem. 265:5855–5861, 1990; Swiss–Prot accession No. P17635, 1990.*
Yueh et al., Biochim. Biophys. Acta 1350:267–271, 1997; GenBank accession No. U59453, 1996.*
Belmouden et al., *Genomics* 39: 348–358, 1997 "Recombinational and Physical Mapping of the Locus for Primary Open–Angle Glaucoma (GLC1A) on Chromosome 1q23–q25".
Cashman et al., *Environmental Health Perspectives*, vol. 104, Supp. 1: 23–40, Mar. 1996 "Pharmacokinetics and Molecular Detoxication".
Chumakov et al., *Nature*, vol. 377 (Supp): 175–183, Sep. 28, 1995 "A YAC contig map of the human genome".
Gasser, *Exp Toxic Pathol* 48: 467–470, 1996 "The flavin–containing monooxygenase system".

(List continued on next page.)

*Primary Examiner*—Ponnathapu Achutamurthy
*Assistant Examiner*—Delia Ramirez
(74) *Attorney, Agent, or Firm*—Saliwanchik, Lloyd & Saliwanchik

(57) ABSTRACT

The present invention concerns, in particular, human flavin-containing monooxygenase 2 (hFMO2), and another human enzyme of the FMO, hFMOx family, their nucleotide and polypeptide sequences. The present invention also concerns vectors for cloning and/or expression containing said nucleotide sequences and cells transformed by these vectors and method for preparing said polypeptides. The invention further concerns methods for selecting compounds and of diagnosing predisposition to pathologies and/or deficiencies related to FMO's and pharmaceutical compositions containing said compounds for treating and/or preventing these pathologies.

10 Claims, 1 Drawing Sheet

OTHER PUBLICATIONS

Hines et al., *Toxicology and Applied Pharmacology* 125: 1–6, 1994 "The Mammalian Flavin–Containing Monooxygenases: Molecular Characterization and Regulation of Expression".

Larsen–Su et al., *Drug Metabolism And Disposition*, vol. 24, No. 9: 927–931, 1996 "Dietary Indole–3–Carbinol Inhibits FMO Activity And The Expression of Flavin–Containing Monooxygenase Form 1 In Rat Liver And Intestine".

Lawton et al., *Archives Of Biochemistry And Biophysics*, vol. 308, No. 1: 254–257, 1994 "A Nomenclature for the Mammalian Flavin–Containing Monooxygenase Gene Family Based on Amino Acid Sequence Identities".

Lomri et al., *Proc. Natl. Acad. Sci. USA* 92: 9910, 1995 Correction: "Molecular Cloning of the Flavin–Containing Monooxygenase (form II) CDNA from Human Liver".

McCombie et al., *Genomics* 34: 426–429, 1996 "Localization of Human Flavin–Containing Monooxygenase Genes FMO2 and FMO5 to Chromosome 1q".

Park et al., *Chem. Res. Toxicol.* 5:193–201, 1992 "Flavin–Containing Monooxygenase–Dependent Stereoselective S–Oxygenation and Cytotoxicity of Cysteine S–Conjugates and Mercapturates".

Phillips et al., *Chemico–Biological Interactions* 96: 17–32, 1995 "The molecular biology of the flavin–containing monooxygenases of man".

Poulsen et al., *Chemico–Biological Interactions* 96: 57–73, 1995 "Multisubstrate flavin–containing monooxygenases: applications of mechanism to specificity".

Schwartzman et al., *Proc. Natl. Acad. Sci. USA* 84: 8125–8129, Nov. 1987 "12(R)–Hydroxyicosatetraenoic acid: A cytochrome P450–dependent arachidonate metabolite that inhibits Na+, K+–ATPase in the cornea".

Schwartzman et al., *Current Eye Research*, vol. 6, No. 4: 623–630, 1987 "Cytochrome P450, drug metabolizing enzymes and arachidonic acid metabolism in bovine ocular tissues".

Sunden et al., *Genome Research* 6: 862–869, 1996 "Fine Mapping of the Autosomal Dominant Juvenile Open Angle Glaucoma (GLCIA) Region and Evaluation of Candidate Genes".

Ziegler, *Annu. Rev. Pharmacol. Toxicol.*, 33: 179–199, 1993 "Recent Studies On The Structure And Function Of Multisubstrate Flavin–Containing Monooxygenases".

Ziegler, *Drug Metabolism Reviews*, 19: 1–32, 1988 "Flavin–Containing Monooxygenases: Catalytic Mechanism And Substrate Specificities".

GENBANK Accession No. L37080, Homo sapiens flavin containing monooxygenase 5 (HUMFMO5A) mRNA, complete cds. Posted on GENBANK Jun. 2, 1995.

GENBANK Accession No. M64082, Human flavin–containing monooxygenase (HUMFMO1) mRNA, complete cds. Posted on GENBANK Nov. 8, 1994.

GENBANK Accession No. M83772, Human flavin–containing monooxygenase form II (HUMMOXYII) mRNA, complete cds. Posted on GENBANK Jan. 30, 1996.

GENBANK Accession No. U59453, Macaca mulatta flavin–containing monooxygenase form 2 (MM59453) mRNA., complete cds. Posted on GENBANK Jun. 25, 1996.

GENBANK Accession No. Y09267, H. sapiens mRNA for flavin–containing monooxygenase 2 (HSFMO2). Posted on GENBANK Feb. 6, 1997.

GENBANK Accession No. Z11737, H. sapiens mRNA for flavin–containing monooxygenase 4 (HSFLMON2R). Posted on GENBANK Aug. 18, 1994.

* cited by examiner

SEQUENCE LISTING

<160> NUMBER OF SEQ ID NOS: 14

<210> SEQ ID NO 1
<211> LENGTH: 26016
<212> TYPE: DNA
<213> ORGANISM: Homo sapiens
<220> FEATURE:
<223> OTHER INFORMATION: genomic

<400> SEQUENCE: 1

```
catcagttat ccctggagga taactaagcc atctgcctcc atcatctttt aagggttcag      60
tcagtttaaa actttgcttc tatacctagg tattttcttt tctctgtatg ttggtcaggt     120
```

```
acaattattt ttaacagggc ttccatcaat atcataacta cctagagaag acattgcaaa      180
gataaaattg gagaattgtt aacaggctgt taacaaaatg tgtacccaac tgccaatgaa      240
gtggcttgat ttttttcttt ttttaaaatt tttcttttgt atcctttttat tttatttact    300 tatttttttag agacacagtc tcgctctgtt acccaggctg gcgtacaatg gcacaatcat    360
agcccactgc agtctcgacc tccagggcct caagcaatcc tcccacctca gccttccaag     420
tagctgagac tacaagtgca tgctgccatg cctgactgat ttttttgtttt ttgcagagat   480 gaagtctcac tatgttgccc agtctgacct tgaactccta gcaataccct accctggcct    540
cccaaactgc tgggattaca ggcatgagcc actgtgcctg gccttttttc atttttaactg   600 agaaatgtgt tcagctcttt tgttccttag tcattgatca tcacttttgt tatatctgtt    660
agtcttgtca tagagttgct gcacttatta cacagagaag gcctttttatc acgaccaatt  720 tatttttagga aatttcaggg aaaacgtttt tctagaacac cttatttgac attataaaac   780
aactcttcac tcttgcactc cagacctccc tttccagttt tctttttctc catagtggtc    840
atcaccactt gttttatttt attgatgggc tgtctggctc cctcaactgc aaagtaaact    900
ccacaaaggc agagagtttt gtctctttta ttcattgctg tacctgcatc acttagaaag    960
tttctggcac ctaggaagtg ttcagtaaat atttattgaa taagtttatg taaaacgtct   1020
cagactcctt agagaaactg gtcttttggg gttggagaat aaagttcttt acctcatcag   1080
ttagactcta tctaaggtac acgagggctt gctagtctcc taagttagtc tgctaataaa    1140 tgttaacccct aataactgaa attattagca gaggtaatta tccagttcta tatcaaggca   1200
aaaagacagc agtggataga aagatcttag aagtcccact aggttcatcc aagccaccat   1260
acacataggc agaaaaatca aaataagata tgagcctgga cagggtgagc aatctgggaa    1320
aagatgaaca cagtatgcta ggacccagaa atcatcaagt ctatgaaaac taagccagaa    1380
cacaaatgtg aattccataa gatcaggaac ataatctgtc ttgttcatcc aggcatggta    1440
atctgccaga aatagtgctt aactgcaaga actgaatatt tgttagataa ttaaaccatc    1500
aactaaatga gattcatgca accatgaaaa atgctgctat aggtacacaa tattgatata    1560
ctagaaagtt aaaaaatcaa gttggaaatt agactattcc atttctgttt gtgtgtatgt    1620
atctacaaat aggtggaagg ataccaaaa atgtcaacag cagttacctc tgggtggtga    1680
ggagtaatct taaccttgtt atttatccct atatgttcat ttgtgaatga atatttatta    1740
catcattata aaaaggattt ttaaactatc tgtatgttta agagtatatg ttgctactat    1800
gtaagagtat atgctgttac tgtaaagaca ttgcattact actgttgacc tcagagcacg    1860
cgcctcttgc ctaattctag gactcctaac taagtctttg gagtttcagc tggaagaatg    1920
ctggaggaat acggaactcc tcccatttct cacagccacc tccaactctt aaaaacgctt    1980
ccaactgcct cccagcacac aaccaaggga gaaaactatt ctgtcaaaga dacggtgcca    2040
aaaggcaaaa acaaaggtaa ggatgatcgc tggggaaaga agctgaaaag gaaaagctca    2100
gaactctagc tggaaatttg gctcacatcc ctagtatgtt actgcatagt ctggcttttgt   2160 tcaatgggtc gcttttaaat attaaagcta gatgtaagca aggtttgcaa caaagtccat    2220
aagaaactca gcttttctca aaggcaagaa gagagcagga ttttttgactg gctctttatt   2280 caatagtgct gcttattaaa ttaccactgc tacaatgttt aaagccaatt acctgagcac    2340
atcataagga ttctccttacc ggttgtccca gttaagtaat gttgattgat caactccttg    2400
acaggagctg atggcaaaga aggtagctgt gattggagct ggggtcagtg gcctaatttc    2460
tctgaagtgc tgtgtggatg agggacttga gcccacttgc tttgagagaa ctgaagatat    2520
```

```
tggaggagtg tggaggttca agtaagtga gattttcttg ggtcttgaac aggttgtgtt      2580
gttatttcag ggtgaatcac agttactgat gggtcatatt gagaaattta ttaaacaact      2640
ctgatcagat tttatttcta tttattgatg tggccataat ggaactgaag tcataggctg      2700
gcatctctcc cccagtcaat actaacccaa cccaggtagc tgacccaggc atgtaaaaga      2760
tctcttcttt tggattcagc aattgtctta cagcccatac ttctgtcatt ctttaatacg      2820
ctaatattag agaacatttt acaaaaatag aagtaacagg gattcttctc aagatatcac      2880
ttctgtttca attattaaac caaatgcttc tttagagacc atgctcttat cattactatt      2940
tttctctgac aaatgaagca tgtttgttta ctgagcttta tcaatgacat tctagtataa      3000
ctgctgtgaa actctttgtt aaatatgttt tattaaattt attctattaa tcaaaccaaa      3060
atattgataa tgctatttgt ctgtattagt ccattctcat gctgctatga gaaatactg       3120 agactgggtg atttataaag gaaagaggtt taattgactc ccagttccac aatgctgggg      3180
aggactcagg aaatttacaa tcatggcagt gggaaagaga ggtgctgagc aaggggggaa      3240 aagccccctta taaaaccatc agatctcatt agaacgcact cactatcatg agaacagcat      3300
gagggtagct gccccccttga ttcaattacc tacccccacc aggtccttcc caagacatgt      3360
ggggattgtg ggaactacaa ttcaatatga gatttggatg gggacacaaa gctaaaccat      3420
gtcactgtcc ttaaaaattt gtataaaact tagaaagttg catagatagc tataaggagt      3480
tacaattatt ccttcccaca acctctcaat aggtagtagc ttaccacctt ctagctgtga      3540
gatcttgagc aagttattta catcctgtgt ttcaatttac tcagttataa atggatataa      3600
taacaggaaa gtgtgattat ctcatagtgc tatttttgaag attaagggag ataattcata      3660
taaagaactt agataagttc cggactcata gagttcaata aatgttagct actaataata      3720
actatatatt ttatagatga gcaaactgaa agtgagggag gttaagtgag atggccaggg      3780
ccacacaact ggaggaactg gccttcaaac cacggcctac gtgacttcta aacagataag      3840
ccctgactta caaccatgcc ctaacttgca ttccttgctca aaaagattaa acaaaagttt       3900
aagttcagaa cccaaaagca atgactttag aattatgtaa tcaggtatcc ctgagatatt      3960
aaaacacata agaatattcc aaatgggagc aaaaggtttg aatacatgaa aatcaaactc      4020
atatcagcag agaccatata aagggctctc actgcaggct gactagttag gaggatggca      4080
aggtgatcca ggacctgcgc atgctttgtc agttcaaatt gaatctcatg ccaacagcga      4140
tcttttttaa catgtaacat taggtgtctc aggtacacat gaccataaac cacacctgga      4200
gggtttcttt tattttcttt ttaatatttt tctgagacag ggtcctactc tgtcacccag      4260
gctaccatgc ccagccatgg agagtttctt aaagatactg attcctttgg ttaaacctgc      4320
caccaaaaaa aaaaaaaaaa aaaaaaaaaa atactgattt gtgggcactc catcccaaat      4380
ctatggaatc aaaatcttct gggggttttt aataaacatc tcaaatgaat cctatgataa      4440
gacaaatttg gtaattgtta cacaaacacc taatttaaaa atctgatcat tctactatct      4500
aaacacactc agagttaatg agggagaagg gagaaattga ttcttctgta agacaggtag      4560
ctttgcaaaa aggaaaacag cttaaatcac attcatttct tattaaaagc tgatgattaa      4620
tatcatttta gttttttcctg ggatggtgat ataatatggt ggtcattcct gtcttaacca      4680
aagatatttt tgtccactct aggttcacat gtagatttca gctggaattt ttttttttt       4740 ttttttttgc tcccaggtag attcttaacc taaacaagaa atgtagaaat tacagttggt      4800
ccttggtata tgcaggagat tggctccaca acctccctcc cccagtatac caaaatcctt      4860
```

-continued

```
gcatactcac atcccacaga tttattgtca gcaaaagaga tgagagttag tttgaacagt    4920
ctgccaacaa tatgatttga tgaattctag gaaggtattt tctgcagtaa aatatttctc    4980
caactatcct tttgccagta tctaaaattt cagattagag ataacttcct attcactaga    5040
aaaactggat taaaacctga ttaattaggc tttattgaat attaagggtt aagtatataa    5100
ctgtggaact tgtaacagta tcacatttca aatttctctt aaaactatat ccaatagagg    5160
aatgtaaact attgtctcca ctcaacgaag tcaaagagtc caaagagtct ccctgcagag    5220
tgaaacataa aataagcaaa atttcatagg ctgcctgcac tacggctatg tgagggtttt    5280
ggttaccagg tgactgggag tttccaagaa ggatgctggg agccccatgc tcttccctgg    5340
gaaactttgc cttttcacta ctctaccatc cagaagcaat tttttaaatg ggttattat    5400
taattttcgt atttacacaa ctcctactga gattacttaa catatttggt ggtgacaagt    5460
taacaataaa taagtaaatt taagaatcct tgtcctatac ccaacccaga caatagagtt    5520
cttccagact ctccagcacc ccctagtggc acatatggac catgggacgg gtaggtaatt    5580
agcatatatt tttcgttctg tttccagcaa cgggaagcac ttggcaagca tcaccttctt    5640
ttcttcgcaa tactgctagg aagtatgtat tatgattatc tttatttaca tattaagaag    5700
aaacagtttt cagataaaga atttgctcag gggaacatag gtggcgggag aaaaaaaacg    5760
agggtttaca atttcggagc tctcacactt aataaccttg ctgaagtatt gatagaggaa    5820
aacatgatct tctttcagcc gctaaccttc tctgtttcct ttattgttcc taataccttg    5880
tattcacgtg ggagttacca tgtacatttt ttttcctgtg ggttttcttt taatatttgg    5940
atttggatct cctccttttc cagatgtata tgtttagtta ttttaattt catgtaatac    6000
tctctagaca tatctcaatc ttggttttct tcctctaagt tcaatctgaa atatcacttt    6060
ctctcttaaa tttggctccc ccaagatcca acattccaaa catattgcca atgagtgtat    6120
accttttagc ttgaaagcag cagaaaaaaa gtggtaaata cctgagccag gaacttaat    6180
taggggggttc tatcagtgat caaggccagt gatcaaggga gacaccagcc taatgaaaga    6240
tgacagaaga tagcaatact ctaatagaga tgtggttcac aaagttcatt gtgcagaagc    6300
agctagggag agcttctaaa atacagaaat ctgagcccgt cttttttctt tcttttttt    6360
ttttttttt tttgagatgg agtctcgctc tgttgcccag gctggagggc agtagcgcaa    6420
tctcagctca ctgcaacctc catccccggg ttcaagcga tttagctggg attacagcct    6480
tgtgccacca cacatctgga cccatcttct aatgcaactg gtccactgac tggcatttgg    6540
gaattgcaat tttgcctcta attgtaggac aaggaagtaa gaagagtttt aatcatattc    6600
aattcaagta atggagcaga tagatgtaag gtccatccga aagagtgaaa tgatagaatc    6660
acagaatatt cttaaagaaa ggcaattta ttctttctaa ctgcttatgg taactaccca    6720
tgaaagcaaa aatattgatt ggtaagggtc aatataatga tgtttcacga agaaaaagtt    6780
taatttgtaa gttttgtaa ttcacattta taataaataa atctgtttct gctttataaa    6840
tttcctcact tgagtagatt aaatattacc cttataatct tctttaaact tactgtttac    6900
aacctttta ttgtcatgaa gtcaaacata aacttcaatt cagctcgtga tcaaaagatc    6960
ataaattcta aataagtgct atctgaatta acttggtttg ctagagtttt ctgcacattct    7020
gaaaattcta tattagaaga attctttatt atatgataat ttatgttaaa caaattatag    7080
caaattctac acataaggaa attcagacta tatttatgct taattatcca ggcagtagta    7140
gtacttaagt aaatatgtga gttaaattta ctgttttga aaactgtgcc tctgtcctcc    7200
tcttgattga caataaaccc tctgtctcca cttttcacatc tccaaagttc aagtgcattt    7260
```

```
taatacaata taacaataag caccataaag atataaacta tgtttgtact gttagcatct    7320
tatccctaaa tccaagctca ggccctggtc agttcaagca tttgatacat acttgtctat    7380
taaatcaaca ttaatcatct cttcataact aggaaaacta ggccaatttt acccagattt    7440
gtctaaatac acagatgcct acttcagcaa actaaatgta gaaggaagca catatgaaga    7500 caaggggtc ttttttagct gctatttacc aattaaccca acaataaaag tttatcactt     7560
ggctgggcgc ggtggctcac gcctgtaatc ccagcacttt gggaggctga ggcaggtgga    7620
tcacctgagg tcgggagttc gagaccagcc tgaccaaaat ggagaaaccc caactctact    7680
aaaaatacaa aattagccgg gcatggtggc gcatacctgt aatcccagct actcaggagg    7740
ctgaggcagg agaatcactt gaacccaaga cggggaggtt gcagtgagcc gagatcatga    7800
cattgcactc cagcctgggc aacaagagca aaattctgtc tcaaaaaaaa aaagggatt     7860 atcacttgat cttcagaaaa atagtgaggt cattattgtt tgctgacaga ctacacaagt    7920
aaaatctccc aaaggccagt tttgccctgg ccctaagatt actgtagggc ctcagacatc    7980
aaatcagttc ttctcatcac tcaaaattcc cttaaaattg acctgacaga gaagccaacc    8040
acatttttaa gccaaattgt tgggtctttt aaaaactagc attttggctg tagtataaca    8100
gtcttagttt aactgattca aaactatggc tggcttagta aatttaacgc tagtggccaa    8160
taataacaga aaagagataa atattcttaa gtatgtattt tgagccaggg attctgctaa    8220
gtactttatt cactctcatt aaagccttga aacaattgtt gcatgtttaa gttattaatg    8280
agccccattt tacagaggaa aatgaggaaa ctgacctatg taacttgctc atggtcacaa    8340
gccattaaag gtggcagaat taggatatca atccagtcgg tgtgactcca gaaccctcct    8400
atttactcta tactactcat aaaattattt ggtcttgggg ctgggcgcag tggctcatac    8460
ctgtaatccc agcactttag ggggttgagg tgggtggatt gcttgagctc aggagttttta   8520 gacctgcctg ggcaacatgg taagacctca tctctacaaa aaaaaaaaaa aaaaaatac    8580 aaaaaattag ccggtgtagt ggcacgcgcc tgtagtccca gctacttggg aggttgaggt    8640
gggaagatca cctgagccca ggaggttgat gctgccgtga ccataatca tgtcactgca     8700 ttccagcttg ggccacagag tgagaccctg tctcaaaaat aataataata atctggtctt    8760
gagaaaaaat agtattttt tcttcataaa atatttccca ttttgagaac ttgattaaga     8820
aactcattgt cttgccaatg acattacatt caatcatgct gaaacatcca gaaatagttt    8880
acacatcagt ttgacatcag tattatgcaa tttgaagcca ctgtttgaaa ataaaaacac    8940
tgtaccgtga tttgtttatc cagagttcag attattatat ccttgtatat gagacagaaa    9000
cccccttgta ttcagtgca aactctcttt ggatcttaat atgtatagtt aacaataata     9060
ccatactaca ttctaactac ctagaaagct agcataactt aacctgatta acttttacca    9120
agttacttga aattatagca aagttaccat ttaaatcttg attctggcca ggtgcagtgg    9180
atgaaccaag catggtggtg cctgtaatcc cagcactttg ggaggctgag gcgggtggat    9240
cacgaggtca ggagattgag accattctgg ttaacacagt gaaaccatct ctactaaaaa    9300
atacacacaa aaaaattag ccgggcgtgg tggcaggcac ctgtagtccc agctactcag    9360
gaggctgagg caggagaatg ccgtggacct gggaggcgga cttgcagtga gccaagatca    9420
cgccactgca cttcagcctg ggtgacagag cgagactctg tctcaaaaaa aaaaaaaga    9480 tttgattcta tcagtctact cacctttata gcttgacaat gattgatttg tgtaaaagga    9540
ttcaaatcaa aatttgcaaa ctcccttcct ccaaaggtac tcatttata atactgaaat     9600
```

```
tctctattat gttctctgcc cagtgtccca gggtttattg gtttctaaag aggtagtggg      9660
tatatacagc ctccccaagg ggaatttagg aagtaagctg gttgtcacaa agactggcat      9720
taaataggta gagacctagg atgctaatat cttgcaatgt gccaaaataa ttgtccctgt      9780
ccccaacctc accattgcca atattacccc taccccctcac agtgagcgtc acaggcaggc     9840
aacaaactgg tgtcgtcaca gaatgattga tggaacacat agactgcatt cattacctaa     9900
acattgtcgt cacactgcag caaccaaaga caatcgcatt acccagggggt tagatgtagg    9960 aagagtaaaa aacaaaaaat ttttgaatgc gtaattatca ctaattattt tatttgatcc    10020
ttcaggagaa tgtggaagat ggccgagcaa gtatctatca atctgtcgtt accaacacca    10080
gcaaagaaat gtcctgtttc agtgactttc caatgcctga agattttcca aacttcctgc    10140
ataattctaa acttctggaa tatttcagga tttttgctaa aaaatttgat ctgctaaaat    10200
atattcagtt ccaggtattg tatttttggg gaaatgggtt tctctgcatt agttcagctc    10260
atatttagat agaaaagtta ctctgataat gaaagcaatt atgaatgaag tatcccattc    10320
taagtatttg ttgaaatata acagcctcat ataaaaccca aaagtagtg tcattaccct     10380 tggtattata gattatatac attaattgaa gaggaaaatc atctgttaaa attaaaggtt    10440
tgaataataa tatattgatg tcaaaacttt ttttttttt tttctccctg agacagagtc     10500
tcactctgtt gctcaggctg gagtgcagtg gcatgatctc agctcactgc aacctctgcc    10560
ttccaggctc aagtgattct cctgcctcgg cctccagagt agctgggatt acaggcacac    10620
atcaccatgc ctggttcatt tttgtatttt tggtagggac gaggtttcac catttgggcc    10680
aggctggtct cgaactcctg acctcaagtg atccacccgc ctcggccccc caaagtgctg    10740
ggattacagg tgtgaaccac cacacccagc ctcaaaaatt catttaaaact aatatctgtt   10800 atcattgaat acacctagct tcatttgcct tgaaagggcg tataccaaaa ttaaattgct    10860
gttttgtttt cttagcttct tcatagaaat gggatttctt agatgtgtat taaataaatt    10920
cattggtctc tgttcatact agaaggctgt gggaagtatt tgcttatcat ttttttctga    10980
atgcaatctc ttacaaccta agatggcca gatcattttg aaaaacactt ggaattacct    11040
tttcctgtgc ttcctcaaaa tcaacaaaaa gcaatatttt aattaagcat gctgaatttt    11100
tatcaatggt ctatactttg agaaatagct actatgctta gaaataaaa tataaatcac     11160 atttcttggc caggtatggt gattcatgtt tgtaatccca gcactttggg aggctgaggc    11220
aggaagatca cttgaaccca agagtctgag accaacctgg gcaatacagt gaaaatctgt    11280
ctctacaaaa aattttttaaa agattatcca ggcatgttga tacccacctg tggtcccagc    11340
tattctagac tgagaaggga ggatcgcttg agcctgggag gtcaaagctg caataagtgg    11400
tgattgtgcc actgcactcc agcctgggca acagtgtgag accctgtctc aaagtaaata    11460
actaacattg ctggataaat aactgttagt gaggcttatt tttaatacat gtcattttct    11520
tagtaattct aatactaggc ttatataata tcaacttaca atagtaaatt ttggtgaaaa    11580
tttgtattta taaattccat taaaatgtcc agttctacct aatgtagttt ttcaccaatt    11640
cctggtagat ctaacttgtg aataacagat tatgtatacc agaaggtttt gtaactttgt    11700
gcacttaact atcaatctac ttaacaaata tattgccttt ttatgatata taacttctat    11760
tccattcttt taaagatcat gttagagtcg caaggaagtc atttctcttg gttattgtgt    11820
tactgctact tttgtttctt ggagagtgaa gagggggttgg gaagaaaggt ttctgttttat   11880 tggtctctga gttggtgtaa gtcataggtg ttagagctca actcgagaag caggcaaact    11940
gtaacaagcc ctgttgctta tgattgtcaa tgtaatctac atcagtgctt ctcaaacttt    12000
```

```
aatgtggaca tgaatcacct ggatatcttg ttaaaaatgt aggttctaat ttaataggta    12060
tggggtaagt tctgaaattc tgcatttctg acaagcttcc aagtgatact gaagatcctg    12120
atcctcaaat cacattttga atagcaagga tctacagcac ttagttaata tactactttg    12180
aactaccatc tgaaatcttt tctttcatct gaaaactgcc cagatattta aagcccttt     12240 acaagatttc tactaatatt ccatatacat ttttaaattg agacagctta aaaattacca    12300
acccagcagt tggaaaaata tctgaaaatt tgagatatat aaaagactaa aatacttgca    12360
aatgagaagc atgccattcc tctagcatta taaactttgc ttccacttga catcgtttct    12420
taatccagca gatatgaaac atttatgtac aattttaaaa attaacagac ctccagtgag    12480
ctacatttaa aaaaatcaat gaaccaataa atcattttat tcaaataaga tcatgaactg    12540
tcttgctcac atgatgtact ctgttttaaa aatagcaaat gttaaaaact atcattcagt    12600
ggaatgctga ccatgtgtca ggcactctgc aaagtgtttt gcgtgaaata tcttctctaa    12660
tacaaagtcc acaagaggc ggctacataa acgttcctg acatatgcca attgcatgat     12720
cacttgaatt attggtttgt ttccttgttc agattatcaa ataacaaaca gagagaagtt    12780 cttaaaaga aagatatat atttggtgat agagcattgt aatgagaatg tacatgccat      12840
ggtaaactat ttgtgtattc agggagttaa aggaagacaa aggttttaa atggggaaaa     12900 aatacaatta cataattgtt ttgaaataat tatataaaga gcaataacaa gggtgatgcc    12960
agtctgagat tggacagtta ctgagcagat gttcttgtag aagtcatttt tgtgtaagat    13020
tatgatggtc tttgtgtaag gtggtggttt ttgtagtttt tgttatcagg cacacatcat    13080
gagaacccgc tctttctggc ctttcccaat tctatttgtc gggtttctta acattagtga    13140
ctccatctag attctgacag ttttcatgag aacttgcttt tcttttctct ctcaagtcct    13200
tattcagtat tcagcaccct taacagatta gtcccactgc tgagtcaggc ctcttgcatg    13260
aagcagcaat gagaaagaca cacttggcca atgttatcct ggagtaattc tcaatgatgc    13320
cttctctgtg tttcttcaag acaactgtcc ttagtgtgag aaaatgtcca gatttctcat    13380
cctctggcca atggaaggtt gtcactcaga gcaacggcaa ggagcagagt gctgtctttg    13440
acgcagttat ggtttgcagt ggccaccaca ttctacctca tatcccactg aagtcatttc    13500
caggtgagac ccgctgggat tcccagcttt ttggagtagg tttccaggta ctttatatgt    13560
agtttggatt gacaagcagg attcattgct gcaactgggc agaacttggc tcaataagat    13620
tgagacagag ctagaaagat gaaagacacc aaacatcatc tttgtttcta ttggcctctg    13680
agtcttcatc acacatagat ctcagagcca acttccttgg aagtcactaa gtccttggca    13740
taattttaga gaattcacat caaactggtt ctctgttgga gaggcccttt tagccatgtg    13800
cctgcgttgg ccttttttcta ccctgccaaa caccgagcct ttttcacagg gccatactca   13860
cacacaaggg gagagctcct agaaagaaat gctttgcaag ttagtgatgg ggagagaagt    13920
gcaggaatag aaccctgcat ccagctgttc tggtccaccc aagtctttcc tcagagaaca    13980
cacttctttc ccaaggccct taggaaaata tgtaatatag tggttcatag tccaggcctc    14040
atattagaat cacctgggga gcttctaaag ccctgatggc ctggagacct accccaaag    14100 attcaaacac tatggagtag ggttagagca atgaaagttt gctcaggtga ttttaatata   14160
cagtcaggat taaggcctgc tcatctaaag caattgttct caaatagagt cacctggagg   14220
gcttttgaaa gcacaaattg ctaggcccca ccctccatat ttctgattca ataggtgcta   14280
tggcttgaat gtcctgtcca aaactcatat tgagattaat ccccaatggg gcagtatgaa   14340
```

```
gaggtggggc ctttaagagg tgattgagta gtaagagctc tgccctcaag aatggattaa    14400
gccatttgtg gataaatagg ttaatggatt attgggttac acaggagtgg aactggtggc    14460
tttataagaa gaggaagaga gacctgagct agcatgttag catgcttggc tccctcacca    14520
tacaatgccc tatgctgcct tgggactctt cagagtccaa accagcaaga aggctttcag    14580
cagacgcagc ccttcaacct tgacttctca gcctccacaa ttgtgtgcca gaagaaataa    14640
cttccttccc ctataaaata ttcggtttca gatattttgt taaaacaat agaagacaaa     14700 ttaagacagt agctctggca tgaggctgag aatttgcatt tctaacacca ggcaatgctg    14760
atattgctgg ccatgtgacc acactttgag aaccaataat ctaaagattc tttcaagcaa    14820
ccccaccatc aatggcaaat actttataaa gtcatgtgtt tccgtgaagt gtaaaagtag    14880
taactaggaa aggacacaga agaagcttgt ctgtgattaa ccaccagcaa gtcactgatt    14940
tacacaatat ggaaaccaac tcctatgtgc ctggttttta gttttagttt ttgtttactt    15000
tttgaaaata agattgctaa attgtattct aactattaca caattataat aatagcactt    15060
cataatgtgc ttaagaaata tttaagagta tctgataagt gatttttttt tttttttgaga    15120 tggagtctca ctgtcaccca gactggagtg cagtggcacg atctcagctc actgcaacct    15180
ccacaacctc catcttccag gttcaagcaa ttctcctgcc tcagcctccc aagtagctgg    15240
gattacaagt gcacgaccac ccctggctaa ttttgtatt tttagtagag agagcttcat     15300
catgttggcc aggctggttt caaattcctg acctcagttg atccgcctgc cttggcctcc    15360
caaagtgctg ggattacagg tgtgagccac cacaccttgc ctaatatgtg atattaaagg    15420
gtcaaatgtc attatatagt ccaaaatagt atataatagg caggcagaag acagtatctg    15480
gtcctgctgt gttcatcacc atttatttgt ctctgataga gacaaactgc agccgtaagc    15540
tgcagcctct gaaataaaaa atcaaccccct ttggtcctgt tttttgttt gtttttgtt     15600 ttgtttttggt gttgtgacag tctcactctg tcacccagac tggagtgcag tgactcaatc    15660
aggggtcact gcattcttta cttcccaagc tcaagcaatc ttcccacctc agtcacccga    15720
gtagctggga ccacaggcat gcacaaccat gcccagctaa tttttgtatt ttttgtagat    15780
acagggtttc actatgctgc tcaggctggt ctcaaactcc tgggctcaat caacctgcct    15840
aggcctccca aagcgctggg attacaggcc ccacctggtc tggtacctaa actttcttat    15900
gtgctttact cctatagaga agaggcaaaa caattattaa ctccagaaag gaaaagctgg    15960
caatgcagtt ttattgaaat tagcttgaca tagttgctct ggagctcaca gacttctctc    16020
ttcttccccc tgaaggtatg gagaggttca aaggccaata tttccatagc cgccaataca    16080
agcatccaga tggatctgag ggaaaacgca tcctggtgat tggaatggga aactcgggct    16140
cagatattgc tgttgagctg agtaagaatg ctgctcaggt gtgatgctct ctgcttacca    16200
tgtacctgga ggggaggaag tggggatgcc atactgagag accccagcca tataatcgcg    16260
gctccaatcc tcattaacta gttggttggt agcgcattgt ggcatcatag aaaatctgga    16320
agtcaagaaa ccactttacc tcctagctct gtcactaacc agccatgaat cctagagtga    16380
ttcatttcac ttctctggga gatggctccc tcattttaa aatgggaact tttgaccaga     16440
tgattttcca tataagaggc ctttcatcaa catggctcac tgcagccttg acctcctggg    16500
ctccaatctt cctgtcatct cagcctcctg agtagctggg actacaggca catgccacac    16560
cacactcagc taattttcat atatttgtag agatgagggt cttgccatgt tgcccagggt    16620
agtctaaaac tcctgaactc aagcaatctg cccgcctcag cctcccaaag tgctgggatt    16680
acaggcatgc acaaccacac ccagccaaga ggccttgttt ctacctggat gtttaatgag    16740
```

```
aggttaatct gttcatattc tggagggtgg cttttagaaa tttagtgtgt atttgaatta   16800
tatttgaaat atagataacc ttcagttacc caaatattat gaaagaaag attaaataga    16860 tagtaggtct ctcaactaaa atcatagata tttaggtgct tcctgaggcc ttctaaccac   16920
tgtcttcttt gcacctgctc aggaatgaca ccagctgagc tgccaaagag tcaaacattc   16980
attacatgat gatgctgctg acagtggtgg tcaggaatag caaaaactaa actccttctg   17040
caaggacaga cctaggcaaa gaagggaaaa tcactaaaca tcctttccca aagtattccc   17100
tctcaagaag gcctgaacca gatgcccaat cactcttacc ctagctcttt cagcctgatg   17160
tctctggcca cccagggctt accatggccc tgtgcacaac caacaaatca tttccatcct   17220
aagtcttaca ctttcaggac tctagatacc cagtggcaaa agttacaagc aaacatgaca   17280
cccgcccagc aggttaatga agggttata ctgggacctg tcagagtcat ctatcagtca    17340
gttagttagt gccagcccgg gaacagagca ggtcactaac accggaaaga gacttactag   17400
acccaataag tcttcacttt gtgaaaataa acctcttgtc acttatcacc tcagtgtgaa   17460
gaacaagtga ggaggcagga actgtgacag cctggagaag agcagagctg gaaaatgaga   17520
gtaccagctc taggctcttt catgctacga atacccgcaa agccttagga acagagtgta   17580
atggggcagt atgtgaggag ctaatatagc agtcagccaa gtgaagatcc atcctagact   17640
acttcacgtt gtcagaccag tgatttggat ttagatctct tcattccaaa gatatcaaat   17700
cttagatggc aagaaccagt tccttgtatg ggtcttgccc tacaggaaga cttatggtgt   17760
gagattcaat attaagaaac taccttggct ctatttgcat gccttacagc ttcttaaaca   17820
atcttttgca cagagtgcaa aagactttgt ttccatctcc ctctatcagt gtaaatgcca   17880
ctagatgccc ccttttagg aggtacttca ctttgaggtc aatcatcttt aaaacagagc    17940
ctcagtaaat tctggggcta tgcatgtgat acatcaccta cataatagat tcctcctaaa   18000
tataatgtta taatcataca tttccaggat tatactcatt catctgcact aatctcttca   18060
atatttatta gagtaacaac ataaatctat aactatgata aaacctctta cacagagtaa   18120
tatactctca agccttctgt gaaaagacta accagagact ttacaggagc tatacatgct   18180
aggaacggaa ctaggcgcat ctgcaaaact tgaaattaca acctgaactc accaaaattc   18240
tgagtgtgca ctgctctgtt aaaagaaatt caccttcata aggttacagc accctctacc   18300
acaatccaaa agcaccactc aagatcatat gggatggtgc tgcatcattg tattagtcca   18360
ttctcaacgc tgctatgtag acatacccga gactgggtaa ttcataaaga aaagaggttt   18420
aattgactta cagtttggca tggctgggga agcctcagga aactaacaat catgacggaa   18480
tgcacctctt tacgaggctg caggagaaag aatgagagcg actggggaac cccttataaa   18540
accatcagat ctcgtgagaa cttactccct attaggagaa cagcatggca gaaacctccc   18600
ccatgattga attatctcca cctggtcctg cccttgacac gtgggggatta ttataattta   18660 aggtgagatg tgggtaggga cacacagcca aaccatatta gtcatttaca tacttctgac   18720
caaaaaccaa atctctggcc tttgacctaa acatgcgtc tcagagaaag cagcctgagc    18780
ctaaatcctc atgtttctct cactgttgca gctagtgtca ttaaggcagg ttagaccacc   18840
ctgctgtagg gagggtcaca acagaaaaag agtgaatcaa acgggcagag cataccattt   18900
gaaacatggt ttgctcctga gaaagaagag gggacagtaa gtaatggaaa gagacactaa   18960
tgaaaatatt tttgtatcta atatctaatc aaagtattgc caagtcagcc tataagggca   19020
acggcaggag aaattcagaa cataggtata taccacacac agaccagcaa tataggaatg   19080
```

-continued

```
cttggtatag gtgctacttc acaagctagg aatgtaaggc ccatccccac aaaatttgtc      19140
tccaaattct ggtttactcc agacataagg cactgtatga aactcctctc ttccagccta      19200
actttataac ttaacagcta gcagtactta tcacttgcca ggcaatattt caagtacttt      19260
atatatacca cctcatttaa tctacacaag aatgccatga ggtaggtact gttaataccc      19320
ccattttaca gagagagaaa ctgaggcaca gagagattga ataattcaa ccatggcaac       19380 acagattgaa atagttcacc cacagtagtg tgattgggat tcaaacccaa gcagtctgta      19440
tccaaacctc tcaagtaaat tggttacctt gcaagtgaat cttatgtgtt tatcaagtat      19500
agccttaaac aaaaacttat tgcatggtat gtaaaaattt aagaagcagt tcaagtatgc      19560
atttggccaa tgggggagta acagcaaaca cagcaaaata tacatttgaa aagagattaa      19620
atgtacattt tggaaacaag ggaaatctta ataaacaagg taaagaatac acctgaaaga      19680
ggattcagat gtgcacttga agagaaagag aatcacagta taagttcaga gtttttaact      19740
tttaaaatac attacaagca ctgtgtctca tgcctgtaat cccagcactt tgggaggctg      19800
cggcaggagg attgcttaag cccagaaatt tgagaccgac ctgggcaaca taatgagacc      19860
gtctctacaa aaaaattgtt tgaattagct ggatgtggtg gtacatgtct gatactgagg      19920
tgggaggatc acttgagcct gggaggtcga gactgcaatg agctatgact gcacaactgc      19980
agtccagcct gagtgacaga gcaagaccct gtctcacaca cacacacaca cacacacaca      20040
cacacacaca caaataaaag tcttttaagt atggaaggaa gattatttcc cctgttattc      20100
tccatccagg gatattcaga tgcatataca cttatacttg tgtagtcact aggctataat      20160
cgcacatttc caaggattat aatcattcta cctgcactat agaagaaact taggtgagtg      20220
gaaaacatga gaggagggag ggaggaactt tctcttaagg agcagcaaac cacaactgta      20280
aacatgggaa agacttgtgg attttatcat cagagttagc ccaaagactt tctcgtgtct      20340
ccatgaagtt ctcaagattt tgttgcagtc ttcctgcatc agtgtaaatg ccactgggta      20400 cccctatttta ggaggtactt tacattgagg tcaatcatct ttaaaacaga acctctgtaa      20460
attctggggc tacacatgtg atacatgacc ttcatagtag attcctccta aacgggacaa      20520
tgccctaatt taaactgcat ttctttttgc ttgccaggtt tttatcagca ccaggcatgg      20580
cacctgggtc atgagccgta tctctgaaga tggctatcct tgggactcag tgttccacac      20640
ccggtttcgt tctatgctcc gcaatgtact gccacgaaca gctgtaaaat ggatgataga      20700
acaacagatg aatcggtggt tcaaccatga aaattatggc cttgagcctc aaaacaagta      20760
gagttatttt gcttttttaa tggtatactc gttggtgagc aaagttgtct gaaggtgtct      20820
cccttaacaa agattcaaat tgctaacacg gtagttaaaa ctacaatcta acaatatgag      20880
tatcttatag gtcctggagt ttagcttcta aatttggtct gtatgccttt aaaaaatact      20940
taagaagatg aagcagaagt gttataagct gctccagaaa gcaaaactag gggagaactt      21000
tctaataccc agagttatct aacattggag aaaactgttt caagagatta cgacctgcct      21060
ttcagagggg tgtggtggga acatgtaatt tctccatcta ataatttatg ctttgctaac      21120
cctatagcat gaaggttctt cccatgggaa acctttgaaa acacattcct ttttctttgc      21180
taaaagacaa atctctgttg acgtcaaagt tatatgtcag tgatttaagc acaagcaaat      21240
gttatgaatg gttcttttgc tttagttgtt acaggcttct tcccttaaaa aaacagaaga      21300
gctttagaat cttttaacaa atgcctgccg tgcaactacc atattctaag atctgacata      21360
agtgccacgt atcgtctatt aaaaaaagaa aagaaaatg ttctcaaatc tacaaaaaaa      21420
ataagcggac tttgcatcaa catccatgct attactaaca gagactccat ggatatttgg      21480
```

```
gattaacaaa tatcaccaaa cctaatttta tacattaatt ttcacattga tcccttcata    21540
gatttcaaaa ctagtggaaa tttagcaaat tttttcttat gatcaaatag gggttaaata    21600
aaacagcaaa ataataaaag ctagatagca tgaaaaaggt taaaaacaga aatggtataa    21660
taaccaccat aatacttggg gattgaccat aggcacaggc attttgtcta agcccttggg    21720
gatgcttcct tccttaaaat ctctttcact cacgttgcct acatgttttc ccttatttat    21780
tgacaagaga tatttgtgac atgagaatta agtcagaaaa taaggatttg cacagacaac    21840
cagttaagtt agagttttac agatatttga aaagcccttt tattttcaga gccgtaccc    21900 aaaaatatca agagggttca agattcctca gcaaatgatc cttcagaatg ttttttcttct  21960 gtatgtctca gatacattat gaaggaacct gtactaaatg atgatgtccc aagtcgtcta    22020
ctctgtggag ccatcaaggt gaaatctaca gtgaaagagc tcacagaaac ttctgccatc    22080
tttgaggatg aacagtggga ggagaacatt gatgtcatca ttttgcaac aggatatagt     22140 ttctcttttc ccttccttga agattcactc gttaaagtag agaataatat ggtctcactg    22200
tataaataca tattccccgc tcacctggac aagtcaaccc tcgcgtgcat tggtctcatc    22260
cagcccctag gttccatttt cccaactgct gaacttcaag ctcgttgggt gacaagagtt    22320
ttcaaaggta agtgtgtagg caggtgagtg gctaagcgtt tcagatctgg tgaagtttat    22380
caataatgat aagaaggttg cctgagataa aaaggttgcc aagaaaaagt ttgacaacct    22440
tggctgctct cacaagacta acattctaaa agttactgg agaattcaaa gaataacaaa     22500
tacaggaatt tagtaataat aaatacctgc aatcatcctt ttaaaatatt agacagtcaa    22560
gagaatttca actggcataa agctaagtgc atgttaactt ttctttgaat cgtgagagat    22620
aagtttaaga aaaagatctg tctcctggtt ttacctctgt gttgtttaaa aattcctcag    22680
catatctgca aatcaatttta actcttaata cttgagcagc tcaacctcac aaatccctac   22740
aagttataaa attattaaaa ggtttctttc tgggtgtctg tgtagcactt catactcctc    22800
agaacggtgt tacctccctg cctccagggt tcaattctgt tcagcaaaag cttactgaat    22860
accttgccct gtgctgggaa ctggtgggac agagagaaat ttaaacagat catttcaaca    22920
taacatgaca aatgctttga ttgaataata tatggagtgt tcagggaagg agagaaaggg    22980
cacttatcat ggtagaataa gggaagggca catgataaag gaaaacgtcc tggataactg    23040
catttctcag gggcagaaaa ggggattgcc tgaacaaaag catagagtca atgatgcata    23100
tggaagggca catgctattt gacattgcta gagcatgacg tatgaggcag agagagatga    23160
gccattactc ttggagaaga aggagacagg acacaggaat ttttaagac atgctatgga    23220 gcttagatta taaattatag atcagttctt cccaaatatg gctacatatg aaaatcatct    23280
gatggatcct tagggaccct gattaagtaa gactggccaa gggacctgga atctgcattt    23340
tagaaagctc ttcagcccgg ggcaccaatg aagggttata agcaaggaac aggcattagc    23400
agatttacac ttcagataga ttgtttcagc agtagtgtgg aatatagatt tgaaagtggg    23460
gaaagactac agcctcaggg atgaaagaga aagctactga aatagcctat gctaaaatat    23520
gatgcatcct gggccagggc agagatacaa agtggaaagg aagccataaa tgtgagaaat    23580
cattaaggga aaaatcagca tgacattatg attggttcaa tgtgggaaag tcagagaaat    23640
agagaggaat ctaggaggac ttacagatct ctggcattgg aaaccaggtg gacagtagtg    23700
ctgtgaatac agagggggtg tgcagaaaat gatgcaagtc tggacaggag ggcttcagtg    23760
aggagctcag gtctggacta cttgaacatg agatgtctga tgactctagg caaggggact    23820
```

-continued

```
tgaccatatt tcaacacatc caaagctcag gggacacttg tgggcaggcg atggagtcat   23880
gagcacacag taataacttc tgcatcaatc tttccctatc tctactgccc tactctcatc   23940
tctcaccagg tttatttcaa cagcctcttt actggtctcc ccagctttgg gcttgcctcc   24000
ctggagtcca ttttcctaaa ttcagcagcc agacagatct ttccaaaaaa taaatctgat   24060
cttctcactt cattcagaat actcttccac tgatttgatt tggggcctcc tgtcaccttc   24120
aggatagagc ccaaaccact agtcatggct gccaggctcc cagacacact tccctttttcc  24180 agcctcttct cttggccctc tccacttgta gtccatgccg tagactgtgc acctggaca   24240 gtgtcacata gagtgctatg ggggtggcac cccctgaagt tcaacagcac ggaagccctg   24300
actggtatga catggttcaa tgtccagagt ttaattttaa gaatcaacaa ctagacaaag   24360
taatgatatt gactcaaact tactattcaa accaaccttt tattccttag gcttgtgtag   24420
cctgccctca gagagaacta tgatgatgga cattatcaaa aggaatgaaa aaagaattga   24480
cctgtaagaa ttttttttaa ttctttacat gaagcagtgt ttctcaaagt acagtgatct   24540
aactacttac aagaaccacc tagctgcctg ataaaatgca aatttctggg ctatagccca   24600
gatgattgaa tcagaaactc cgtgtgtgag gctaaaaagt tgcatttta tcttcttcct    24660 aagcgattct tatacatact aggttaagaa ccaaatactt aaagataaga attgtaccaa   24720
atcagagcac ttctccttgg cttaatttca tttcagtttt atatgatgcc tatgtcagat   24780
tccataactt ctcaagccac ctacactctg tggttagaga gggaatggga tgagacagtg   24840
gtggtgatag tagcttgaat agctgtgaaa agttagagaa tccccatcag aataaattag   24900
gaaggggttg gtgtgaaggt tcaaggattt gtactttgtg atgaggtaaa atgaggttca   24960
acagtgatcg agtaccttg gaaagttgat ttggggctta catcaggtgt aaagagtttt    25020
ctcatgttca aattcaaatt tacctaagat tgattgagta tctactatac gccatccaga   25080
ctgccaggta ctttagtaat ttaacaagca aatattaagc atctcctttg agcaagacac   25140
caagctatgc tttcatatgc attatctcat gaattcctgc agccgccctg gctagcatgt   25200
acttgcctgg agatttgcca ccgcttaaaa aatgccaaac aatggttacc aatcttgtca   25260
catttctaga gcatccatga attcatggct ctttatttga gggcgtattc tcaatctgag   25320
atatgagcct cctggtatga taaactcaaa cttttccacca gagattcatt gaaaactcat   25380
tcacatattc actcattcct tcattccttt agcagttttg aatgcctaat attctagaaa   25440
acttagaaca ttctgtgaac attcccttt tactttcttc actaaggttt ggagaaagcc    25500
agagccagac gttgcagacc aattatgttg actacttgga cgagctcgcc ttagagatag   25560
gtgcgaagcc agatttctgc tctctcttgt tcaaagatcc taaactggct gtgagactct   25620
atttcggacc ctgcaactcc tattagtatc gcctggttgg gcctgggcaa tgggaaggag   25680
ccagaaatgc catcttcacc cagaagcaaa gaatactgaa gccactcaag actcgggccc   25740
tgaaggattc atctaatttc tcagtttctt ttctgttgaa aatcctgggc cttcttgctg   25800
ttgttgtggc ctttttttgc caacttcaat ggtcctagtc agcataatgc tttgggcttt   25860
attatcttgt cagtcactac ctcctaaaga aaaaaaaaa ggctagaaga aaaaacatta   25920
cattcatgtt ctaattatag attttagagt taggtagtac aggtaagggg gaaattgtaa   25980
agaattagca gaattaggca tatgtacaaa accaaa                              26016
```

<210> SEQ ID NO 2
<211> LENGTH: 1731
<212> TYPE: DNA
<213> ORGANISM: Homo sapiens

```
<220> FEATURE:
<221> NAME/KEY: misc_feature
<222> LOCATION: (1)...(1731)
<223> OTHER INFORMATION: n = A,T,C or G
<223> OTHER INFORMATION: cDNA

<400> SEQUENCE: 2
```

| | | | | | |
|---|---|---|---|---|---|
| aaccaaggga | gaaaactatt | ctgtcaaaga | gacggtgcca | aaaggcaaaa | acaaaggagc      60 |
| tgatggcaaa | gaaggtagct | gtgattggag | ctggggtcag | tggcctaatt | tctctgaagt     120 |
| gctgtgtgga | tgagggactt | gagcccactt | gctttgagag | aactgaagat | attggaggag     180 |
| tgtggaggtt | caagagaat | gtggaagatg | gccgagcaag | tatctatcaa | tctgtcgtta     240 |
| ccaacaccag | caaagaaatg | tcctgtttca | gtgactttcc | aatgcctgaa | gattttccaa     300 |
| acttcctgca | taattctaaa | cttctggaat | atttcaggat | ttttgctaaa | aaatttgatc     360 |
| tgctaaaata | tattcagttc | cagacaactg | tccttagtgt | gagaaaatgt | ccagatttct     420 |
| catcctctgg | ccaatggaag | gttgtcactc | agagcaacgg | caaggagcag | agtgctgtct     480 |
| ttgacgcagt | tatggtttgc | agtggccacc | acattctacc | tcatatccca | ctgaagtcat     540 |
| tccaggtat | ggagaggttc | aaaggccaat | atttccatag | ccgccaatac | aagcatccag     600 |
| atggatctga | gggaaaacgc | atcctggtga | ttggaatggg | aaactcgggc | tcagatattg     660 |
| ctgttgagct | gagtaagaat | gctgctcagg | ttttatcag | caccaggcat | ggcacctggg     720 |
| tcatgagccg | tatctctgaa | gatggctatc | cttgggactc | agtgttccac | acccggtttc     780 |
| gttctatgct | ccgcaatgta | ctgccacgaa | cagctgtaaa | atggatgata | gaacaacaga     840 |
| tgaatcggtg | gttcaaccat | gaaaattatg | ccttgagcc | tcaaaacaaa | tacattatga     900 |
| aggaacctgt | actaaatgat | gatgtcccaa | gtcgtctact | ctgtggagcc | atcaaggtga     960 |
| aatctacagt | gaaagagctc | acagaaactt | ctgccatctt | tgaggatgga | acagtggagg    1020 |
| agaacattga | tgtcatcatt | tttgcaacag | gatatagttt | ctcttttccc | ttccttgaag    1080 |
| attcactcgt | taaagtagag | aataatatgg | tctcactgta | taaatacata | ttccccgctc    1140 |
| acctggacaa | gtcaaccctc | gcgtgcattg | gtctcatcca | gccctaggt | tccattttcc    1200 |
| caactgctga | acttcaagct | cgttgggtga | caagagtttt | caaaggcttg | tgtagcctgc    1260 |
| cctcagagaa | aactatgatg | atggacatta | tcaaaaggaa | tgaaaaaaga | attgacctgt    1320 |
| ttggagaaag | ccagagccag | acgttgcaga | ccaattatgt | tgactacttg | gacgagctcg    1380 |
| ccttagagat | aggtgcgaag | ccagatttct | gctctctctt | gttcaaagat | cctaaactgg    1440 |
| ctgtgagact | ctatttcgga | ccctgcaact | cctatnagta | tcgcctggtt | gggcctgggc    1500 |
| aatgggaagg | agccagaaat | gccatcttca | cccagaagca | aagaatactg | aagccactca    1560 |
| agactcgggc | cctgaaggat | tcatctaatt | tctcagtttc | ttttctgttg | aaaatcctgg    1620 |
| gccttcttgc | tgttgttgtg | gcttttttt | gccaacttca | atggtcctag | tcagcataat    1680 |
| gctttgggct | ttattatctt | gtcagtcact | acctcctaaa | gaaaaaaaa | a               1731 |

```
<210> SEQ ID NO 3
<211> LENGTH: 535
<212> TYPE: PRT
<213> ORGANISM: Homo sapiens
<220> FEATURE:
<221> NAME/KEY: UNSURE
<222> LOCATION: (1)...(535)
<223> OTHER INFORMATION: Xaa = Any Amino Acid

<400> SEQUENCE: 3

Met Ala Lys Lys Val Ala Val Ile Gly Ala Gly Val Ser Gly Leu Ile
```

-continued

```
  1               5                    10                   15
Ser Leu Lys Cys Cys Val Asp Glu Gly Leu Pro Thr Cys Phe Glu
                20                  25                  30

Arg Thr Glu Asp Ile Gly Gly Val Trp Arg Phe Lys Glu Asn Val Glu
            35                  40                  45

Asp Gly Arg Ala Ser Ile Tyr Gln Ser Val Val Thr Asn Thr Ser Lys
 50                      55                  60

Glu Met Ser Cys Phe Ser Asp Phe Pro Met Pro Glu Asp Phe Pro Asn
 65                  70                  75                  80

Phe Leu His Asn Ser Lys Leu Leu Glu Tyr Phe Arg Ile Phe Ala Lys
                 85                  90                  95

Lys Phe Asp Leu Leu Lys Tyr Ile Gln Phe Gln Thr Thr Val Leu Ser
            100                 105                 110

Val Arg Lys Cys Pro Asp Phe Ser Ser Gly Gln Trp Lys Val Val
            115                 120                 125

Thr Gln Ser Asn Gly Lys Glu Gln Ser Ala Val Phe Asp Ala Val Met
        130                 135                 140

Val Cys Ser Gly His His Ile Leu Pro His Ile Pro Leu Lys Ser Phe
145                 150                 155                 160

Pro Gly Met Glu Arg Phe Lys Gly Gln Tyr Phe His Ser Arg Gln Tyr
                165                 170                 175

Lys His Pro Asp Gly Ser Glu Gly Lys Arg Ile Leu Val Ile Gly Met
            180                 185                 190

Gly Asn Ser Gly Ser Asp Ile Ala Val Glu Leu Ser Lys Asn Ala Ala
        195                 200                 205

Gln Val Phe Ile Ser Thr Arg His Gly Thr Trp Val Met Ser Arg Ile
    210                 215                 220

Ser Glu Asp Gly Tyr Pro Trp Asp Ser Val Phe His Thr Arg Phe Arg
225                 230                 235                 240

Ser Met Leu Arg Asn Val Leu Pro Arg Thr Ala Val Lys Trp Met Ile
                245                 250                 255

Glu Gln Gln Met Asn Arg Trp Phe Asn His Glu Asn Tyr Gly Leu Glu
            260                 265                 270

Pro Gln Asn Lys Tyr Ile Met Lys Glu Pro Val Leu Asn Asp Asp Val
        275                 280                 285

Pro Ser Arg Leu Leu Cys Gly Ala Ile Lys Val Lys Ser Thr Val Lys
290                 295                 300

Glu Leu Thr Glu Thr Ser Ala Ile Phe Glu Asp Gly Thr Val Glu Glu
305                 310                 315                 320

Asn Ile Asp Val Ile Ile Phe Ala Thr Gly Tyr Ser Phe Ser Phe Pro
                325                 330                 335

Phe Leu Glu Asp Ser Leu Val Lys Val Glu Asn Asn Met Val Ser Leu
            340                 345                 350

Tyr Lys Tyr Ile Phe Pro Ala His Leu Asp Lys Ser Thr Leu Ala Cys
        355                 360                 365

Ile Gly Leu Ile Gln Pro Leu Gly Ser Ile Phe Pro Thr Ala Glu Leu
    370                 375                 380

Gln Ala Arg Trp Val Thr Arg Val Phe Lys Gly Leu Cys Ser Leu Pro
385                 390                 395                 400

Ser Glu Arg Thr Met Met Met Asp Ile Ile Lys Arg Asn Glu Lys Arg
                405                 410                 415

Ile Asp Leu Phe Gly Glu Ser Gln Ser Gln Thr Leu Gln Thr Asn Tyr
            420                 425                 430
```

```
Val Asp Tyr Leu Asp Glu Leu Ala Leu Glu Ile Gly Ala Lys Pro Asp
        435                 440                 445

Phe Cys Ser Leu Leu Phe Lys Asp Pro Lys Leu Ala Val Arg Leu Tyr
    450                 455                 460

Phe Gly Pro Cys Asn Ser Tyr Xaa Tyr Arg Leu Val Gly Pro Gly Gln
465                 470                 475                 480

Trp Glu Gly Phe Arg Asn Ala Ile Phe Thr Gln Lys Gln Arg Ile Leu
                485                 490                 495

Lys Pro Leu Lys Thr Arg Ala Leu Lys Asp Ser Ser Asn Phe Ser Val
            500                 505                 510

Ser Phe Leu Leu Lys Ile Leu Gly Leu Leu Ala Val Val Val Ala Phe
        515                 520                 525

Phe Cys Gln Leu Gln Trp Ser
    530                 535

<210> SEQ ID NO 4
<211> LENGTH: 25464
<212> TYPE: DNA
<213> ORGANISM: Homo sapiens
<220> FEATURE: UNSURE
<223> OTHER INFORMATION: genomic

<400> SEQUENCE: 4
tccagtcctg cagcaacctc ctagttcctg ctctttcagc tctttgacct tttgcaagca      60
cctaattccc tgtagtatat accttcttc atgatatata gtgttttta tctcctgcac      120 taaatcatga gcatatgcat ataaatcata atatgaaatc ttaaaaacag aagtactttt     180
gctgaggcat taagcatata atcagtcagc aggtccccaa acatctaatt cctgaatatc     240
tcatatatcc tgtctccatt atccattcct ctaatgctac tctaatttaa gtcctcagtc     300
tctctggcct agattgttga aataacatcc tgggttttg gtctccttga ttctagtcac     360
catcctctct agcctccagg tgaatctgat cttgtctgat gttgtcactt ccttgttcaa     420
aattctcgaa tggacaaccg taatccagaa ggtagtatcc aaacctgtga ttgtggcact     480
tcagtatcct tcataaccta tgtcctgcat gtttaaccca tattttgcta ttcccatcac     540
ttatggtcca gcaaaactga actaattgta gttcccccat cacgtgttct acttttcta     600 tgcattttca catattttc tctctgcctt ttttctattt cttgtccctt atctgtctgg     660
aaaacatcta ttcttcctc aagactcagc tgtcttctca cactccttga agcctctctt     720
tcctcctcca agtggaccta gattttctt cctacatgct agcactacac tgaaccatac     780
ttccactgtg acatttatca tctccctcaa cactagactt catggttcca gatgaaaagc     840
actgtgtctt ctcaccttg aatcccccaa aagactatta taatgcatga catatagtag     900
gctgtcagta cagtgaaagg aatggccaga ggaaggaaag gagggaaaca gaagcagaaa     960
ggacaggtat agaagccgga gggagccaga gacaaggttc agagaccaca attctgtctt    1020
ttgagttcac tagtttttaca agctcatcta taagcgttag ttcagcaact cagatcaggc    1080
cctaagtttc cagaaatttg agctactttt cactgttggc acaacaaaac gtttcattat    1140
agtccaggtg catagccttt gtttatatat tctatatttc caaagcaaac ataaatgaaa    1200
gaatcattgt tcccctaatc tcccaggagt ttcaccttac agctccagtg gccatggcag    1260
tcactgtttt atattttttg taacaagaac caaagacttc attcttcctt tttcctaccc    1320
ctttcttttt acttcaccca tgcctcccct gttcttctct tatccctacc acactcgtcc    1380
ttctctttca gattttacta tggctctata ccattaaaaa tacaagaaaa aaaggaatt    1440
```

```
ttactttaag aataactcct cccccttccc cagttttcac atcaaaagac attgttaaat   1500
gccattctct tccacatttc gagaactgct gattctctgg ggagagaaag gtgattgctt   1560
aagaggtgaa gtcccttaga gcattcaaaa tgaggagtga ttctgtacag aggatatcat   1620
gcagcaggct ggatgtctag ttccaattcc tttatttgtt acctctgaga ccttgaagaa   1680
gtagtttcta gtctcagcat accaaagcgt catctgcaat tgagagcatt ggattgatga   1740
tcttcaaggt ccttcctgct ctagcattca ctgaatctgc tattttgac atattgaata    1800 atcagaagca gccagtttta gaatcttatt atagcaaaag tggtaaaaat aatgagcata   1860
tactatcaat gtgcatctat gtcttcttat gtttgagtga ggatcctgat acataaacct   1920
tggctgataa tttctactga aaaaaatcgt aagtattaaa gacactcttc tgaagatgtt   1980
ctctccagac tctgctacag gcaatcatga gcaagagggt tggcatcatc ggagctggag   2040
tcagtggctt ggctgccata tggtgctgtc tggaggaggg gctggagccc acttgctttg   2100
aaaggagcga tgatgttgga ggcctgtgga aattctcagt gagtggcaca tcattagaac   2160
accagtggaa ggagatggat tccaatgcaa atcaaatctg atcagttcta attcagattt   2220
agaaggcaga tcacaaaagc tccaaatctg gaaagtaaaa tcttacctct ccaatcatac   2280
taatgcccaa aaaactatt tcataccagc aaaatttgtc ctgaaaagga cattttcagc    2340
tcattaaaca tcatcacctg catggtgaaa tccagatctc caagctgtaa agggcactaa   2400
tgttggtaat tagtcaaaaa tataccatgg gcttcccagg taagtgaaac aattctattc   2460
tttattgctc ttaaatgcca ggaacacgac tagaaaagag acaaacaaac ctggactgag   2520
atcctgaggt cagaagtcct gagttctaat ttcaacttgt aggttttcta ggcagataag   2580
atttcagtcc agttgctttt gtttccctgg acctcaaatg ctcatttgtc aaatgcagag   2640
gatatgattc tataattaac ttatgtctat tgggcagata gaaattatta tagatgatga   2700
ttgtgtgtgc ggctgttgaa tagcctatca gctccaaatc cagagggaaa aattatggtc   2760
tttgccattt gggctcattg tagaaataat ataattagga aatagtcctt gtaaacacat   2820 tttttttttaa atttcaaagc caagtttgga gaaacttcta gttcttctgt cctggatttc   2880
ccagccattg taatcagttg tcgatgatac atatttggct tgaaaacata ttcacatcat   2940
tcatattgta actacttcct gtcctggtct cagttactgc tctgcctgcg ccaatagcct   3000
cctccaatag agtatatcag tgctaactta gaacacattt ttattcttct ccaagctttt   3060
tttaaaaaaa attgtggttt tgtaaccctg aaagcactcc atgagatata aggtcattaa   3120
tttttatttc ccagtagggg gtaatcaaga gttaatattt ttcaagaatt taattttccc   3180
tatttacatt tgctcaggga aatgtggaca gcttagagta aatcataaaa tggctttcta   3240
ccatctccct agtaacaatt aaatgatgct tgagcatcta ttctggtagt ttgtgctaag   3300
tactgggatg acaaatatgg aatataatca ctccttgtaa atggttccat ttcatttgat   3360
taagcaagcc ataatataat tccgtaatcc tttgatagca aatgggcaaa aactcatttg   3420
atagccgaac ctcttctgaa atcgtaaggt taaataccgt gaattggatc aacatgaagc   3480
taagtctcac cttctgttgc acggcagaaa ttttattgca tttgacagat tgctgcccca   3540
gatctcacta ggagtattat ggagcaaaat ccaaaaatgt acacattcca aaatatatct   3600
ggccctaaga cttttaaaat aagagattat ataactacaa caacaagata gaccttgtca   3660
ccatcaattc aatggacgag tgcctcgagc gtttagaaga gggtggacta cggaaatctt   3720
agtaggtcaa agaaaacctc ccacagggat gacacttagc cttgaaggat aaccccagac   3780
```

-continued

```
aagcaaaata gaggaccacc tgtgacacaa ctcctagaga gtgcatttcc caataaagtc    3840
tgcgaatggc actccatagg cctatgcagt cattggcagt gtgccagcac caggttaaga    3900
gagaccaaca atccatgaaa ggcacagaaa aggcaatgaa catggtgtgt gcagagaggg    3960
atccatgagt tatccaatat agccagatca gaaagtttac ttaaggaagc aataatatga    4020
tacaaagatc agtaagattc aaagttggat tctgagttat ccacaagagg aaattcttct    4080
tttccataag gtcatgtcta taagcaaaat tctactcaaa gtcctggtga ggatatggac    4140
ccatacaaat actcaaaact ttagcctcct ccacataccc cagcccttcc ttcttttctt    4200
agaaaagttg cttggcacaa tatataatca gagagggatt ttttttatgt gttacataag    4260
actttatctt gtaagccttt tttagaaggt gttctagcag acagaaacgt ggtaattctg    4320
aacttttcac tatttgcttt ttctgagaaa tgaaaaccaa atgggattta aatactagca    4380
ggctgaatgt gtgttttaag tttcatccac tcctaaatag ggcctcgtgt cctcaaaaga    4440
tttcattact gctgtaataa aagttgctc aacagccagg tgcggtggct catgcctata    4500
atcccagcac tttgggaggc caaagcgggt ggatcacgag aggtcaggag ttcaagatca    4560
gcctggccaa cacagaaaaa ccccatctct actaaaaaca caaaaattag ccaggtgtgg    4620
tggtgggtgc ctgtaatccc agctactcag gaggctgagg caggagaatc tcttgaaccc    4680
aggaggcaga ggttgcagtg acctcagatc atgccactgc actccagcct gggcaataga    4740
gaaagactcc attaaaaaaa aaaaaaatgc ttaccaatag gttagtagca ttttgattgc    4800
aaaagctgaa gccaggacta tttgaacttt ttcccactca tttattcctt tgttcattca    4860
atgaatacat actgtgtact ttatgtgtag ggtactatat taagcataag ctgcagataa    4920
gaggccagcc agcactttaa aagccgtgag aaaacaagta tcagaataac tataagtgac    4980
tatataatta gggcaataag gataatggga ccttagtaaa actaaagatg atttggcagt    5040
agctgagagg gaaggtaaag aaagccatga caaagttgaa ggcaacttt gagcatattt    5100 caagggcata tttagacaag gagatatggg actcataagc agagctggaa taggaaagaa    5160
gatcaaggta aactgcttag atgcatgtac aacattctga aattaacctc tgactttgcc    5220
ctcaagttac ttatgttctc gtgggaaaga tgagagatga acacggttat catccaagac    5280
agatggtgcc cacagctgct tagatctctg gttccagggt aaagctccct cagctagagg    5340
cagagtcaaa gttgaatttc ctccttactg gctcaaacca cacctcatat tgaaataata    5400
aaaatgcatg ctccctggag caactgactt gttatctaat acatttgctt ttttgtgttc    5460
acttggagaa cagtcttttc ggaaaaattc caaggagctg tagtgtacat actcttctct    5520
cctggtgtta taattggctg aggtcaaggg gcaaaaaagc agagattcat tcaagatgga    5580
aatattccaa ggcctagca tctgtttccc agaacagagt cttacattct ttaaccaggc    5640
tccatcccac agttcagccc tgcctccttt caacaggcag ctgaaaaaac ctccttccca    5700
cctctccttc tcacaaccat cagtagaagg cgctagctgt gggtgaaagg gaagcactca    5760
gcctgccaaa ctgctggaca tgagccttca cccttttct gacctccaca aaaattttaa    5820
aaagtttaaa ttcctgtgct tccacgctta tgagaaatac agcaaccatg aatagaggaa    5880
gattatgttt tcaacttgag aaaaaatact gaggctttgg gcagcccccc acttccccac    5940
ggggacacaa tcctctcaac cctttccagc acttttgtt tccctcttcc agaggtcatc    6000
tggtgtgaga gggagataca catcttgaat ccagcagcaa cgtgacattc catctctttc    6060
cccccattgc acaagagtcc cttccggacc tcgggaagca gaagctgcca gctctgaaat    6120
gtattttcaa ggcagcacat tgtgtgcact tttaccctac cctcacaact gagaggaaat    6180
```

-continued

```
gtttattttc aatttagctt ttgactgctt ctaaaaaata agccactttt caattacaca    6240
gaggctttaa aatgaagtgc caagatttaa cacatgttct aagggctctg gtttcctgtg    6300
tttctttggt gaggagtgaa gtccagcaac tggtgagcca agaatagga ttcatttaca     6360
acagagcagt ggttctcaaa gtgtggttcc taaaccagcc acatcagcat caccaggaac    6420
ttgatagaaa tgcaaaccac cccagactcc accccagaca gattgaatcc gaaattctaa    6480
gaatagggcc caagaatcta cggtctaggg agcttccagg cgattctcat tacgccaaag    6540
ctgggaaacc actgcaatat tgggttgttg ccagtgaaga gtttgctaaa ctccaaaagc    6600
aaataaatag gctagaagtc agagcctctt ctagacagtt ttgttttttg ttttttttt     6660
aacctgagta taagatcaga accagtggtg gcacaggaga aagcaaaaac cactaagtgg    6720
ctataaagac agagctaaca ctgagggtaa ttacagtaag aggattcaca tggaaagagc    6780
tccagttctg tgccaggtta cgcgaagggc tttccattcc ttatcttact gagagctttt    6840
aattttgtt tacgctttta aacatgaaaa gggttttagt caaccaagaa ttgaaccact      6900
gtgttcacta agggaacac aattcttggc tttctcttta agctttctta ttctccctag      6960
gaccacacag aagaaggcag agccagcatt taccagtctg tattcacaaa ctcttccaaa    7020
gaaatgatgt gctttccaga cttcccttat ccggatgatt acccaaacta tatacaccac    7080
agcaagctcc aggaatatat aaagacatat gctcaaaaga aggatctttt aagatacata   7140
tagtttgagg taggggtctc ataacttgta ctgttgaaat taagatatgt gtgggttaga   7200
gaaaaaggag gcagcaaact attataaaaa ttagagccaa atgtttgggc acctcagtaa   7260
tcaaatgttg ggtctgatta taaagcattc atgcattgat tttttctctc ctagacttac    7320
tagttcacta gtctctgaga gctttcagac taccttagaa aatggaggca gctagcccat    7380
cattgtccac tttccaccct catgctctga tgttttggaa ataatccaaa atgctttagt    7440
atatattagg aattttgtca gttcaatgcc aatgagttgt ggttcaaaaa accagagcat   7500
ttggtagggt ttctcccatt acattatgaa aaggttaaca acttaaatgg gaaatatagt   7560
cattgccccc atctttaccc actcagttca ttagtttttt tattaaaaag gtgagatttc   7620
agcattgttt ctgcgagaat aatgttttac atttatttgg gactctttat tgagcatttc   7680
tgtctgtatg tttggaactc ttaacctcaa ttaactgctg ctaaatgcag aacacttgca    7740
tatagtggga aaaacaatca gcaaaattat gaaccatggt gatatttaca tcattatttt    7800
acctggagta gccccaaatg tatagttaaa ataaaatttt ccaatagtca ttttattcca    7860
ttcattcatt acattcattt gcttccatta tggtgttaat atcaacaaac attaatgaag   7920
ttcctattgt gtgcttgcat tgtgctatgt gttatatgta aagaaaaag aggtctaaga     7980
cttagctctc aagaagttat ttcaaaataa atatgtaaag agtaagtaaa aagattccag     8040
taacaatttc aatcaaagag aaaattttt aaagctcttt atgatttgtt tataaataaa      8100
acaatgctat ggagatcatg aagcaagagg caacactttg ggggaaggta ttttctagag    8160
gaggtaaaat ttagttgtat ttagtaggtg ttttagataa atgagtggca tgagtaaaat    8220
tagagaggtg ggaaaatgcc ctgctcattt ggagaacagt gggcaaacca agttggttag    8280
gagggagata tatatgctag gatgagatat ggccacatat atcagtaaac tagtgtgtac    8340
tgtgactttg aaaaatagag gattattttg caaccatgta aaagaagtcc aaagaaggga    8400
catccagagc ttatgtgatg gcaccaaagt tatcaaagat tcagcttcac ccatcttagc    8460
acgtggccta catcatgacg tttgccttgt ggtgcaaaac agttgctgaa gcttgagccg    8520
```

-continued

```
tcacatctgc cttctagcaa aaaaaaaaaa aaagtaaaga atgaagggca aaggatgtt    8580
ctctcagctg aatcagctcc ccttttacaa attctcctga aaaactgtc caacattgct    8640
tatatctcac aggccaccct agttgcacag gaacctggaa aatgcatccc ttttctgtgt    8700
atgttgtcgc tccaaacaaa atcagggttc tgttagtaag aatgaaggga gaatggacat   8760
tagggaagca atttgcagaa tatgttccag aaaagtctgt gggaataaca gaaaataaaa   8820
ctaaaagagt aaattggaac aaaattgtat ggacttaata gtaatcgcat tcaaaatgta   8880
gaataagttt tagaggctgt gaagtaacag aaattgagca gtgaattgag cagagaaatt   8940
gagaaatgaa tatagtcctt caggaagatt aatctgacaa gcaggacaaa ggatggcttg   9000
taggaaatgg gaggctgaag acaggctagg tataggttct tgccgtagtc catgcaaggg   9060
agtgataagg acttgaatga aggcagtgtt agcaatcatg gaaagaaagc gtgagattgg   9120
gagataaata ctgtttaaac atgaggcaag gatggagaaa taacaaggaa aacaagtcat   9180
ggatttgaag cataagtggc tgggagtttc atgtcatcat tcaaagaaat aagaaagtca   9240
gaagccagtt tcaaaggaaa tttaagtagg tcaatcaaaa cctgctacat atgaggaagt   9300
attaggtggc cctccagatg gaaaggtcaa gctaaactgg atagaagaga gaccaaggat   9360
agatgtattt gtatattcat accacaaaac ttgctaattt tttttttttt ttttgagac    9420
ggagtctcgc tctgtcgccc aggctggagt gcagtggcgc aatctcggct cactgcaacc   9480
tccgcctccc gggttcacac cattctcctg cctcagcctc ctgagtagct gggactacag   9540
gcgcccgcca ccacgcccgg ctaattttt gtatttttag tagagacggg tttcaccatg     9600
ctagccagga tggtcttgat ctcctgacct cgtcatccac cgcctcggc ctcccaaagt     9660
gctgggatta caggcataag ccaccgcgcc tggccgtaaa gttgctatat ttctaagata   9720
agagtattta tgcagagcaa aagagatgcc aacgatcaaa ccttgagata ttcccatact   9780
tattgagtag atggaagatg aggtcagaaa aggaggaagc catgtcagta gagggtagcc   9840
ataagaaaat aacacagatt tgttatatga catcattcac aaaaatattc agtgtgattt   9900
acccctaaat caactaactt gatgtcaaaa agtaaatgta ctccagtgag taattttct    9960
tgtgagattc aaagactcac tgaagattca ctgtgactcc aattttacta tctttctata  10020
catttctgaa tgaccaagag agctcgtaac aattatttcc tccacagaaa caaggcaaga  10080
aggaaaaaaa ctttcacatg tagaattata aatggaaaaa taaattttct agttttctta  10140
aagaccctgg tttccggtat aaagaaatgt cccagcttct tagtcacggg ccaatggtt   10200
gttgttactg aaaaggatgg gaaacaggaa tctactattt ttgatgctgt aatgatttgt   10260
tcaggacatc acgtataccc caatctgcca acggattcct ttcctggtaa gtttggaaaa   10320
tatataataa tctagggact tatatgcaaa catcaagagt tagaaacata tctttctata  10380
ggtattacat aatgattatt cttagatttc aaaagaaaaa aattaagttt aatgatagga  10440
tatagtaata aatagcctca taagtcctta tgttaaaata atcaaggact gcaagccaga  10500
gatcagacaa acacaagttc ctgtgttaca gacagtaact caaatataag ttctaacagc  10560
acacggggtc tccgagcaca gttacattaa aaaaagtag agtccaactg ccaaatggtt    10620
taaagaaaga cacgtttact tatgttattt ataggagact cctaggtttc taatttcatc  10680
ttcatccaca atttgcaaat aaactttaga aatctcagtg atttgtgtgt gggtacacac   10740
atgggtgtgt gtatagcagc atacttcatt accatccgaa agtggcaaac ctcaaataaa    10800
tacaatatac atggaggctt ccttccattt ttccttcctt ccttgccaca ggaacacaat   10860
ctactcaaag atattagagt ttccatgtct aggtatgatg tccataggcc gaggaaaatt   10920
```

```
aaagagtgaa ggttcaggag gaatataaga ttaaaactct taatgttaac gggcagcata   10980
tttaatgttt atgagcatgg gatcagaaca cctggcctca acttactatt ccactagttc   11040
cttaccactt aacttctttg tctcaatttc ctcttctttt aaaataggga caatagccca   11100
ccatgcaggg atgttatcaa gattaaatag ttaaaacgtg taaagcattt atcagaggat   11160
ctagcccaca gagttaactt aataaatatt aaccattatt attatcgaaa catacattct   11220
catgccttaa gatttttttaa ggaactaaaa gtaagttttta gggggcttaa tgtcaaaaaa   11280
tgctaaatgg ataaatgcac ttcaactagg gaattttttta attacaactg ataataggtt   11340
taaaaagaca caagaaaaac atcttcataa tttctgaaaa tcagttcaaa caacttgcca   11400
tgttccactt aggcctggac cagtttcgag gcaactacct ccatagccgg gattataaga   11460
atccagaagc cttcaagggg aagagggtcc tcgtgattgg tctggggaat tcgggatctg   11520
acattgctgt tgagctcagc cgtctggcta cacaggtaca tgacgtaaag gttttgggaa   11580
ataaacctaa ggtagggctg tgctactaaa tcagtagcca aggcacagag gatggtactt   11640
ctatgtcaca ccacaagaga tccacctctt ctatgtggcc cttcaaatca aggaggactt   11700
gagacatcct ccatgtgaag ccaggtaatg tggcccgtgc tagtaaggaa gtacattcca   11760
ctgaatccag aagtaagtgc atgagtgcgt gtatgtacag atgagtgtgt atgtgtgtat   11820
ttcttgtttt cattttatat tctgatcacc tccaaataga ctagttcctg gtcaggctta   11880 atctttatttt atttaacagt atttattata acgtatcatg caaaaagcac tgtgtttacc   11940
actctgaagt tctgaaagat atgcatgact tggtatttac taacattaat tcaatcaaca   12000
gcagatgctc aacaaatatt gggcacttac tatgcttact atgtgtcaga actatgataa   12060
actaaaaata aatgcataaa taagttagac tagttcctga cttcaagaaa gagtcaatgg   12120
atggagatgg agttgacagg tacacacaga ctatcaccag aggagatggt gagtcttcca   12180
gtagaattag gtgtggcaat agcaacacag ggaaaagaga atctaactta gcctggatga   12240
ggtcaaggaa gacttcccag aggactccaa gctaaatcat gtatcatcga tagaccctaa   12300
agaaacaaca tatttttaag aaaacaggtt ctcaataaat aaattcttaa atggatgtaa   12360
ataaaacctt aattttttaa actaaaaatt cccttcagtt atcacaaagt taaagtctat   12420
tttgcaaaga cggtaaaata gataagcagc cagactcatc tcagggctga ggcggttgcc   12480
atggtttggg ttgctcagga gaagtccttg gggtatgtgt ataggagaa ctggaaaagg   12540 caaccagaga cagagaacag aattaaatcc ttgacatctc gtcagcctaa tttcagctag   12600
agatttagct acacttttcc cacacctagt ccactatcac cagccacaac cactggggct   12660
cactggatca tctggtccct accagacttg ccatcttagt ctatgagtat gtgaagatta   12720
aaccatcaca gttgaacaca gagccctgtt gttcctagag tgatgattct aatcctttca   12780
acaactacac accagccctc aggggcagtg aaagaatcct gtctctacta gtttaaattt   12840
tagactttaa aaaaaatttt ttttatttta agttctggga tacatgtaca gaacatgcat   12900
aggtctgcac atgccatggt ggtttgctgc acctatcaac ccttcatcta gattttaagc   12960
cccacatgca ttaggtattt gtcttaatgc tctccctccc ctagccctcc atcccccga   13020 caggccttgg tgtgtgttgt tccccttcct gtgtccatgt gttctcatga ttcaactcct   13080
gcttatgagt gagaacatgc agtgttcggt tttctgttcc tgtgttagtt tgctgaggat   13140 gatggttttcc agcttcatcc atgtccctgc aaaggacatg aactcattct tttttatggc   13200
tgctagacaa cttatttaga ctcgcctttt aaaagtgttc ctacttggat attgaggaaa   13260
```

```
atgcacggaa gtgcccaaag aagtgtgttg tgtttgctta tttcttacag agtaatgctg   13320
aaatctgtgt tgcttttccc caccaggtca ttatcagtac cagaagtgct tcctgggtca   13380
tgagtcgggt ctgggatgat ggctatcctt gggatatgat gtatgttacc cgctttgcat   13440
cctttctccg gaatgtcctt ccttcattca tctctgactg gttatatgtc cagaagatga   13500
acacgtggtt taagcatgag aactatggcc tgatgccttt aaatgggtac ttaaaaatgg   13560
aaattttttt tattcaaaaa agggggcac tcatttaatg aatttattct ctctagaact   13620
tacttttgtt gtctcattga gcctagaaac attaaactca aggtttcaca ggtgacggaa   13680
tatgcccaga gaccacgtat ggcttggaaa acttattgaa attagtccag tacagaaagg   13740
gtatggaaaa atctgaaatg gagatgacgc aggcagataa atcaccctga catgcatgat   13800
gcatttgtgg tggctacaag ctatagcata gaactttgag gactgaacaa actcaaattg   13860 gttttttggaa gaatatcttg tccgtgctta tgggtgtatg aagacatcaa taataatact   13920
tgcttctcaa gatggttgtg gtattcaata atataaaaat ataaaaattg ctttctaaat   13980
gataaagctt taaaaaaatt ggttcttctt agtctcaatt tttctaatgt gcttcaaagg   14040
agcaaataac aaaatagtgt taatcaacat gtctcagcaa gtaggaagtc tcaaaacaaa   14100
agtgcacact tcctccaccc ctgaaatgtt gacattttg cagaaccatc aggaggcatg   14160
gaacacataa agtaatggag agtcacaact aacgtgccct gtaagattag tcagattcat   14220
ttatttactt ctttatagag acagggccca acatttacta attaggaagt cattccaggt   14280
agaagaatca gcatatcaat agaaaaaaag aatatttaag ttggtaagaa aagaaagaat   14340
tgagaaattt tatctcctgg cccatgctag ccaaaaagtt tcattgtgtt tagagaaaga   14400
tggtaagaaa aaggaggaac tgtaaatcaa aagagcaaat gccagattta ggagctaaac   14460
tgtcagtcca aagcacttat actaccaagt cttgcaggct gctataaccc tttaaaatat   14520
gttgatttta tgcatttaaa attatgttta acactgtggc ttgcttgaca gtagagggtg   14580
ggaggaggaa gagaatcaga aaaaaatact tatcaggtac tatgcttatt acccaggcga   14640
caaaattatc tatacaccaa accctgtgac cacacaattt acttatataa caaccatgg   14700 accccccaaac ctaaaataaa agttttttaaa aattatgttt aatatagtaa gtcccatagc   14760
ttgagctggt taagatttttt tatcttgtaa gagtaactat aaattatatt ttggccttgc   14820
catttagaca attaaaacat agttttagaa attcattcat tctgaaaact aagcttcctt   14880
ttggaaaggg ttccaattac cctaagtttc tggagggaga aagggggagg aaaaacaggt   14940
ttcattgtgg tctatgtttt gctaccttgt aaggtaaaag aagaggttgc aggattagat   15000
aaacagaaaa tgatgtggaa gtatagagac aaatttcagg atttacaagg tttcttttgtg   15060 tctgagatac ttgcaggaaa ttccggaatc tcaaaggaaa cttaaatcaa aatgaaatat   15120
attgtcctga aaatattat tcctagaatt ttggcaacta aaatgcaata tcaaagttgt   15180 tacactttt tgtggacaca gctgatgaaa gaaaaccaaa catggcaata aaacttccca   15240
ccactgcaag tctgatttct ccatgtaaga caagacgtta aagttatgat aatagtgcac   15300
ttataacaac agtgcttgca tgtgccagga actgttttaa gtgctttaag gataattgat   15360
catttaattt tcacaacaac ctatgaggaa gattccatca tcatccccat tttacacata   15420
aagaaacaaa tacagaaaag taacaactag taagagatgg agctaggtta tgaacctggg   15480
ccatctgctt ccagagttgg cgttcttaac cactttagta tgtctataaa ttagttttag   15540
tctcatttag gaaaggaatt gccatgagag aagagagtca gtggcactca tgctgatgtt   15600
taagtgcttg atgttatttc aatgttatgg gctgttgcag gtatttcttg gaaatgagct   15660
```

```
atttacagca agggtgtttg cctctcattg ctgtagttcc ctgagaaaag agcctgtgtt    15720
caatgatgag ctcccatccc gcatcctgtg tggcactctg tccatcaagc ccagtgtgaa    15780
ggagttcacg gaaacctcag ctgtgtttga ggatgggacc atgtttgagg ctatcgactc    15840
tgtcatcttt gcaacaggct atgattattc ctaccccttc cttgatgaga ccatcatgaa    15900
aagcagaaac aatgaggtta ccttgtttaa aggcatcttc cccccactaa tggagaagcc    15960
aaccttggct gtgattggct tggttcagtc ccttggagct gccatcccca cagcagacct    16020
gcaagcctgg tgggctgcta agtatttgc aagtaggtgg gccattctgt ctttcattca    16080
ttttatcaat gaacatttac tgaacacctg ctatatgcaa agcactgtgc tagggataca    16140
atgagaacaa gacaaacatg ttccttgacc tctcaaggct taaaatgggg tgtgggggat    16200
gccataatag gggaaatttg ggggggttct agtgagggga gttggactgt tgcacagagc    16260
aaacagtata caggaagtca taaggtgag ggaaagcatg aaatgtgtaa ggacccagaa    16320
acattttggt ggaagggaat ataaagcaga ggcagggagt ggcaagaaat ataggtttat    16380
aagccacgtt aaagagctta aacttctcat agggattaag gacttcgcaa gattttaagc    16440
aagaaaaaaa tagcagagga taactgcaat gtcaggctac attataaaga ttggaagggc    16500
cctggtgagg gttggaggtg tgccagaaac ctcactggtg tcaacttctg tcagaataac    16560
aaagtcaggc cactctgatt tcatgacaa tcttcttctt ctctccctct actctagacc    16620
tcatggtctc caggggctac aagtatgctt atgtgaggaa atcaagaata tgaggattac    16680
atggagaaag gcaatgtctc aaatatatta atttactcca gtcatactga atattatcat    16740
tattattgaa aagtgttctt ttattcaggt attctccaaa atattgacca atataggtat    16800
aacttaccta acataactaa tccataaaaa cttacactat tggtaattaa caaaccatta    16860
caatcatgga atatatgtat atatattgtc taaaactttg tagataaata aatttctatt    16920
tcaaatacac catgaaagat catcatttaa ataaacccca tcatgaaatc ttttgtaaag    16980
gtgctccctg caaaatactt ctattgcctt tttccttcga aaggcacaac aatgccaaga    17040
gcctgggta ttatgagaag actggatata gttcataaac ctaagaaatt tacatgaagc    17100
aaatggtatc atttatttat tcagcaaata cttactgaac acctactatg tgtcaggctc    17160
taacctggca cttaggacac aacaacaaac gaagcagaac aaaattctgg cctcttactt    17220
tctagcaggg tgtccagcca atatcaatca tagggtacta ccaggttgac ataagacact    17280
aacgatgact gggaaatatt catgcactgc aaatttaga gtaactttct tccactgtta    17340
caaaggcaaa taagctacca tcaccagtta aagaagttg cattgatgta gtgaaattca    17400
caaaaagcta aaacttgtct gctgccccctt aaaacacctt gcatagttgc agaagatgtt    17460
taaaatccta tgcttccttc cattacctca tttaaaatgg cagaaacctt aaagggaact    17520
gttttaccag attctttctt cagagaagtt ttaggaaaag gatacagaaa aaaaggaag    17580
aaattattaa gctattatat gcatgaagtg tactgagcac atatgttgag gattaggtcc    17640
tctataatgt taccgaaata agagactgag tgatttgaag ctacaaatgt ctctgctgtc    17700
actatctcac tacaggccag cttttccaat tcccaaaggt tcattaactt ttcagatctt    17760
tgtttctatg aactggtatt ttgctaaaga tatcaaagac atctccagct cctcttaata    17820
caaaagtttt caggaataca gtttataaaa accaaatgat ttccatcata tgtcattata    17880
tatttctgat ttgtgttttt caatattttt ctcttcattt cttttctaga ctcatgtacc    17940
ctgccaacca cgaatgaaat gatggatgac actgatgaga aaatgggaa aaaactcaag    18000
```

```
tggtaagcag ctaactgtac ttgctaatag agcaagttcc taaaatgtgc ctttatgtgt   18060
agaaaaacat taatatgctt taatattgtc attagtcaga gtttacattt tctgaacact   18120
tgcaataatc aaaaaatgtt tagatagtaa acagtcatca cacttctctt gtgtaactca   18180
agaatagagg ttttctatca gggataattt tgccctccag gtgacatatg caaaatctg    18240 gagacacttt tggtcattgt gagtggagag ggcatgctat cagcatctta tgagtagaga   18300
acagggattc tgctaaccat ccaacaatgc agagcacagt tcaccaaaac aattatctgg   18360
ctcaaaatgt caatagtgct gaggttaaga aacaactcta taaatgacta cagttgacct   18420
ttgaacaaca caggtttgaa ttatatgggt ccacttatac atggattttt tcaattaaca   18480
taatgcagat tgggcatggt ggctcacgcc tgtaatccca gcactttgtg aggctgaggc   18540
gggcggatta cctgaggtca ggagttcgag accagtctgg ccaacatggt aaaaccctgt   18600
ctctactaaa aatacaaaaa aaattagtcg agtgtggtgg tgtgcacctg taatcccagc   18660
tactcgggag gctgaggcag gggaattgct tgaatcaggg aggtggaggt tgcagtgagc   18720
caagatcgcg ccactgcact ctagcctagg tgacagagtg agactccatc tcacaaaaaa   18780
aaaaaaaaaa aatgcaattt tttggagatt tgcagcaatt taaaaactca aggccaggcg   18840
cggtggctca cgcctgtaat cccagcactt cgagaggccg aggcgggtgg atcatgagtt   18900
caggagatca agaccatcct ggctaacatg gtgaaacccc gtctctacta aaaatacacc   18960
aaaattagcc gggcgtggtg gcgggtgcct gtagtcccag ctactcggga cgctgaggca   19020
ggagaatggc gtgaacccag gaggcggact tgcagtgagc ccagattgtg ccactgcact   19080
ccagtctggg caacagagtg agactccgtc tcaaaaaaaa aaaacctcaa agatgaattg   19140
tgtagcctag aaatatttta aaaaattaag aaaagatgc catgtataaa atatttgtag    19200
atactagtct attttatcat ttactaccat aaaatataca caaatctatt attaaaaatt   19260
aaaatttatc aaaactaaat gcatacaaac tcttagacta tacatggcac cattcatagt   19320
caacagaaat gtaaacaaac ataaagatgc aatattgtca taactgcata aaatatagca   19380
cataatgtgc tagtataata attttgcagt cacctcttgt tggtattgca gtgagctcaa   19440
gtgttttgag tatctactta aaatgctgtg tgacattagt catttccacc tgagcagttc   19500
atatctccag taaattctgc ctcacagtaa aaagtgatct ctcaaggttc tcacatattt   19560
ttatcatgtt tagtgcaata ccttaagcct ttaataacac catgggctcc atatgaagtg   19620
tcattaatga tgttggaagt gctcccaaga agcagagaaa agttatgaca ttataataaa   19680
aaaattgagt tgcttaatgt atactataca ttgaggtctg cagctatagt tgcccaccat   19740
ttcaagataa atgaatccag tgcaactatg ccagcaggca tgaaatcttg cacttttttgt  19800 aaaatatctt tttattttgg attgaaaatg cagcttttta tgtgggtgca ggattgctat   19860
aaggaagtat acatatagac tctaatataa tttgagaaaa agtgaagtta ttatatgaca   19920
aagcaaaagg aaggtgaagg atctagagct ggaaaagtta atgccagcaa aggatgattt   19980
gattacatca gaaagagttt ggcttcaaaa atgtcaagat aacaggagac acgcatgctg   20040
ccaaccaaga agaaggagat gaattcccag atgtcattat gaaaatcatt gaggagaaag   20100
gatttctgcc tgaacagatt tttaacacag acaaaagtgc cctattctgg aaaaaaaaaa   20160
aaaaaaaaag ccacaaaggc catttattaa taaggagcag aagtgagcac caagattagg   20220
caggaaagaa taagctaact actgttttgt gcaaatgcag tcagatttat gatcaggatg   20280
gcccctacct atgaagctac cccctcaaac cttgaaggga aaagatgaat atcagcttcc   20340
tatcttttgg ttatacaaga cccttttttct ggattagctc tgtcaatgct ttgtccctga   20400
```

```
agtcagaaag tccttgccaa taagagactg cctttttaaag ttttttttgat atagacaatg    20460 cccctgacca cccagaaccc catgagttca acatggaagg catcgaagta gtctaatttc    20520
ccccaaacac aacattctaa ttcagccttt atatcaggga gtcataagga cctttaaggc    20580
tcatcacata ccatactcta tggaaaagat agtcaatgct gtggaagata acccaacaga    20640
gagaacatca tgaaagtctg gaaggattat accattgaag atgccctaat tgttatagaa    20700
aaagccatga aagccatcaa tcctaaaaca acatatttct cctggagaaa actatgtcca    20760
gatgttatat atgacttcag aggatttaca acagaccagt cacagaaatc atgaaaaga    20820 ttatggatat ggcaaaataa aaaggtgagg gtgaagggtt tcaagatatg gatcatggag    20880
aaattcaaca gctaatagac accactaata gacactttta attccacact agaggaacta    20940
aaagatgact tgatggagat gagtccttcc aaagcagtgc cagatgagaa cgaagacata    21000 gaaaagcca tgccagaaat aaaattgacat tagatcatct ggcagacagg ttccagttat    21060
ttaagacttc ttttgacttc ttttatataa catggaccct tctatgatac aggcactgaa    21120
actaaagcaa atgatagagg aaggattact actatataga aaattttag agaaataaaa    21180 aagcaaagtc agacagaaat tataatatat ttccataatt acaccaatgg gcctgcctct    21240 cctgcccca attctacctc ctccatctct tccgcttctg ccaggcctga acagcaaga    21300 ccaacccctt ctgtttctcc tcctactcct cagcctactc aacataaaga tgataaggat    21360
gaagacattt atgataaacc acttccactt aatgaatagt aaacatattt tttcttcctc    21420
ataattttct taataacatt ttcttttctc catattactt tattgtaaga atagtattta    21480
atacgtatga catataaaat atgtgttaat caactgtttg cattattggt aaggcttcca    21540
gtcaacaggt tattaagagt taagtatttg gggagtcaaa agttatacat ggattttga    21600 ctgcaagagg gctcaatgcc cctaacccct cagttcttcc aaagtcaact gatataggaa    21660
gtttctttac ttttcaagc atttaacatt gcattgatat gtcaacctaa aggaaaacac    21720
tgaggcaaat ttaatataaa aagagaattg atttgggcca agtttgagga ctgcaaccca    21780
ggagcacaga gtcaaattgc cctgaatatg cactccgttg gcagcagtta caagtaggtt    21840
ttttaaagga aatacaaaag agtcaacttc taagttgttt accaagaact tacattaaaa    21900
ttatataagc tattgattgg ctatatactg ttcttcgtat cacaaattct acgaacatga    21960
agatgatgag tgagacagct agtcaggaat aaaaatgcct tttaacaatt gccgccaggc    22020
ttggtagagg gcagcatgac aagtcccata cacgtggctc tctcagcttg ataaattttg    22080
catacctcac atagtgcaaa ctactctgag ctatttttct tctctcacat tgaatgccac    22140
aatgtagtca cccattcagg gcctagagaa gaaagaaat ggaaccctca gattcaacaa    22200
aacctctcct gcacaacttc agccagttga cgaacaactt gcagagttgg gcacttttat    22260
gtgctaacaa ttcatgcagc ttgatacccct ttcctttaga gcccagtaga aataaaaatg    22320
aggaaataga gaggttaaaa tgttcatctt attgcttaaa tgataagctg ctcttcagag    22380
tttcaaaaag caaattacac catattccaa ctaaagaaac tatagaggcg gaaggaggt    22440 gatctctttt ctctctgtca taaaaggtaa tggccaacac ccctataaca aaagacaggt    22500
taacaagaga aaacgtgaca gatttattac gtgcacatgt gtgcatgaga gccttacaaa    22560
acatgaactc aaaggagggc cagatcattc atgtttaaat attctcttca ctggggttag    22620
gggagatgga agtgtaaaag taaatgattt ttcagaggaa attaataagt ccaaagaaca    22680
cagattagac caagtttctc tgggctttgg gggaggtgta atcacccaac agattcatct    22740
```

```
tgctcactgc ccagaaaagc tgatgccctg agaacagcag gttttttccaa tagagagagt   22800
ttaataaaca cacagctgtc agaggcattt gaaccagagt gactccatct tgaatagggg   22860
ctgggtaaaa tgaggctgag acccactagg ctgcattccc aggaggttag gcattcttag   22920
tcacaggatg agaaaagagg ccagcacaag attcaggtca caaagacctg gctgataaaa   22980
caggattcag taacgaagct ggccaaaacc caccaaaacc aagatgatga aaaaagtgac   23040
ctctggtcgt cctcactact cattatatgc tgattataat gaattagcat gctagaagac   23100
actcccacca gcactgtgat agtttacaaa tgccatggca atatcaggaa gttaccctat   23160
atagtctaaa aaggggagga accctcagtt ctgggaactg cccatttctt tcctgtaaaa   23220
cttatgaata atccaccccct tgtttaacat gtaatcaaga agtaactata agtatactca   23280
gttgagcagc ccatgccact gctctgccta tgaagtagcc attctttat tcctttactt    23340
tcttaataaa ctcgctttca ctttatggac tggccctgaa ttctttcttg tgagaggtcc   23400
aagaaccctc ttttggggtc tggccagcta aacggaagga caggagttta ttactactca   23460
aatcagcctc catgaaaatt cagaggctag attttttttaa ggatagtttg gtagtcaggg   23520
gctagggaat ggggaatgct gattggttgg gtcagggatg aaaccatagg gagtcaaagc   23580
ttgtcttctg gtcttcctgg gaggagacca catgacaaga tgaaccagtt taccagtctg   23640
ggtagtgcca gccggcccat cagaatgcag ggtctgaaaa atatcttgag caccaatggt   23700
aggttttata atggtgatgt tatccatagg agcaattggg gacttctgac tgcatgactc   23760
ctgagcccta atttcttatc ttgtggctaa tttgttagtt ctacaaaagc agtctgatct   23820
ccaagcaagg aggggttttg ttttgggaaa gggctgttac catctttgtt tcaaagttaa   23880
actgtaaact aaatgtctcc catagttagc ttggcctatg ctcaggaatg aataatggca   23940
gcttggagat tagaagaaag atggagtaat tacattttttt tttcacatttt ttttcactgt  24000
cacaattttt ttaaaggtga tttcagaggt aacatcacag gacatgggag actaaaggga   24060
ggaaagtatg tcaaacaaag gctgtcctgt tctgcagacg aaacctcaca gaaagcaact   24120
ctcagagtca gtagcctatg atgaaagttt ctctgtcaga cattcagcag tgcctgactc   24180
tcagtctctc tctcctgcaa gttaatcttt cctagagtgg gcaagggagg cctccgagaa   24240
agcctagttt ccatcttctg tttacttcct tttattttct ccacagataa aaatctcctt   24300
cacaaaaggc agcttttcag ggctgtttct gtctgcaggc cctctgaata gccatctcaa   24360
aatctgtcaa cgaagtgtat attttgcagt aaaatatttt ttgttttctt tagtatgaaa   24420
caatttatat tattagatta caggagtatt aaaaccatcc atgatctcac ttttaaacaa   24480
accaatctga aagtctaaca ttggggcaga ttctaagcaa tgtcttataa agaataatta   24540
tgtgttaatg agtaaactaa gttaattagt ctccttaaac cagagggtca gtttactcca   24600
ggccacatgg tcaaaggcaa aagtccaaca ttacatcaaa ctcaaataga gattaggaag   24660
gaggagaaaa gcagctcact tagctaaaga aaaaacaata aattcaattt tgtggaaaag   24720
gagggcataa atggaggtgc tatctaaaat gttatttttc tgaaagaaaa aataagaaat   24780
taatgctcct atttgcaact gtaacactta ttccagtatg ttctcttctt tcttcatgtt   24840
tggccagagc cagactttgc agacagatta catcacatat gtggatgagc tgggctcttt   24900
catagggggcc aagcctaaca taccatggct cttcctgaca gatccccgcc tggccctgga   24960
ggtgtacttt ggcccttgca gcccatacca gtttcgactg atgggaccag ggaagtggga   25020
tggggccaga aatgccatcc tgacccagtg gaaccggaca gtgaagccaa ccaggacaag   25080
agttgtcagt gaagttcagc gaccccatcc cttttacaat ttgcttaaaa tgctttcatt   25140
```

```
cccattactc cttctggctg ttacacttac attttattaa tgagaaagtc tttgaggtct    25200
caaaattcag catagaagtg taatcacaca atacaacaca caccacacat acacacacac    25260
aatcacaaca tagttcctct ctcctttcct gaagatatga aaatcagtct tggcccattt    25320
gaattaaagt ataagtaaaa tggaaaatac tcagcctctc tctctctgtt gggaatctgt    25380
tctctaaaag gcttttcaca tgctgaattg gcaaatttgg ggatgcttaa gataagacag    25440
gaagttgaat aagcatgagc acag                                           25464

<210> SEQ ID NO 5
<211> LENGTH: 1605
<212> TYPE: DNA
<213> ORGANISM: Homo sapiens
<220> FEATURE:
<221> NAME/KEY: misc_feature
<222> LOCATION: (1)...(1605)
<223> OTHER INFORMATION: n = A,T,C or G
<223> OTHER INFORMATION: cDNA

<400> SEQUENCE: 5
gcaatcatga gcaagagggt tggcatcatc ggagctggag tcagtggctt ggctgccata      60
tggtgctgtc tggaggaggg gctggagccc acttgctttg aaaggagcga tgatgttgga     120
ggcctgtgga aattctcaga ccacacagaa gaaggcagag ccagcattta ccagtctgta     180
ttcacaaact cttccaaaga aatgatgtgc tttccagact tcccttatcc ggatgattac     240
ccaaactata tacaccacag caagctccag gaatatataa agacatatgc tcaaaagaag     300
gaacttttaa gatacatana gtttgagacc ctggtttccg gtataaagaa atgtcccagc     360
ttcttagtca cgggccaatg ggttgttgtt actgaaaagg atgggaaaca ggaatctact     420
atttttgatg ctgtaatgat ttgttcagga catcacgtat accccaatct gccaacggat     480
tcctttcctg gcctggacca gtttcgaggc aactacctcc atagccggga ttataagaat     540
ccagaagcct tcaaggggaa gagggtcctc gtgattggtc tggggaattc gggatctgac     600
attgctgttg agctcagccg tctggctaca caggtcatta tcagtaccag aagtgcttcc     660
tgggtcatga gtcgggtctg ggatgatggc tatccttggg atatgatgta tgttacccgc     720
tttgcatcct ttctccggaa tgtccttcct tcattcatct ctgactggtt atatgtccag     780
aagatgaaca cgtggtttaa gcatgagaac tatggcctga tgccttttaaa tggttccctg     840 agaaaagagc ctgtgttcaa tgatgagctc ccatcccgca tcctgtgtgg cactctgtcc     900
atcaagccca gtgtgaagga gttcacggaa acctcagctg tgtttgagga tgggaccatg     960
tttgaggcta tcgactctgt catctttgca acaggctatg attattccta ccccttcctt    1020
gatgagacca tcatgaaaag cagaaacaat gaggttacct tgttttaaagg catcttcccc    1080 ccactaatgg agaagccaac cttggctgtg attggcttgg ttcagtccct tggagctgcc    1140
atccccacag cagacctgca agcctggtgg gctgctaaag tatttgcaaa ctcatgtacc    1200
ctgccaacca cgaatgaaat gatggatgac actgatgaga aaatgggaa aaaactcaag    1260 tggtttggcc agagccagac tttgcagaca gattacatca catatgtgga tgagctgggc    1320
tctttcatag gggccaagcc taacatacca tggctcttcc tgacagatcc ccgcctggcc    1380
ctggaggtgt actttggccc ttgcagccca taccagtttc gactgatggg accagggaag    1440
tgggatgggg ccagaaatgc catcctgacc cagtggaacc ggacagtgaa gccaaccagg    1500
acaagagttg tcagtgaagt tcagcgaccc catcccttt acaatttgct taaaatgctt    1560
tcattcccat tactccttct ggctgttaca cttacatttt attaa                    1605
```

<210> SEQ ID NO 6
<211> LENGTH: 532
<212> TYPE: PRT
<213> ORGANISM: Homo sapiens

<400> SEQUENCE: 6

```
Met Ser Lys Arg Val Gly Ile Ile Gly Ala Gly Val Ser Gly Leu Ala
1               5                  10                  15

Ala Ile Trp Cys Cys Leu Glu Glu Gly Leu Glu Pro Thr Cys Phe Glu
            20                  25                  30

Arg Ser Asp Asp Val Gly Gly Leu Trp Lys Phe Ser Asp His Thr Glu
        35                  40                  45

Glu Gly Arg Ala Ser Ile Tyr Gln Ser Val Phe Thr Asn Ser Ser Lys
    50                  55                  60

Glu Met Met Cys Phe Pro Asp Phe Pro Tyr Pro Asp Asp Tyr Pro Asn
65                  70                  75                  80

Tyr Ile His His Ser Lys Leu Gln Glu Tyr Ile Lys Thr Tyr Ala Gln
                85                  90                  95

Lys Lys Glu Leu Leu Arg Tyr Ile Gln Phe Glu Thr Leu Val Ser Gly
            100                 105                 110

Ile Lys Lys Cys Pro Ser Phe Leu Val Thr Gly Gln Trp Val Val Val
        115                 120                 125

Thr Glu Lys Asp Gly Lys Gln Glu Ser Thr Ile Phe Asp Ala Val Met
130                 135                 140

Ile Cys Ser Gly His His Val Tyr Pro Asn Leu Pro Thr Asp Ser Phe
145                 150                 155                 160

Pro Gly Leu Asp Gln Phe Arg Gly Asn Tyr Leu His Ser Arg Asp Tyr
                165                 170                 175

Lys Asn Pro Glu Ala Phe Lys Gly Lys Arg Val Leu Val Ile Gly Leu
            180                 185                 190

Gly Asn Ser Gly Ser Asp Ile Ala Val Glu Leu Ser Arg Leu Ala Thr
        195                 200                 205

Gln Val Ile Ile Ser Thr Arg Ser Ala Ser Trp Val Met Ser Arg Val
    210                 215                 220

Trp Asp Asp Gly Tyr Pro Trp Asp Met Met Tyr Val Thr Arg Phe Ala
225                 230                 235                 240

Ser Phe Leu Arg Asn Val Leu Pro Ser Phe Ile Ser Asp Trp Leu Tyr
                245                 250                 255

Val Gln Lys Met Asn Thr Trp Phe Lys His Glu Asn Tyr Gly Leu Met
            260                 265                 270

Pro Leu Asn Gly Ser Leu Arg Lys Glu Pro Val Phe Asn Asp Glu Leu
        275                 280                 285

Pro Ser Arg Ile Leu Cys Gly Thr Leu Ser Ile Lys Pro Ser Val Lys
    290                 295                 300

Glu Phe Thr Glu Thr Ser Ala Val Phe Glu Asp Gly Thr Met Phe Glu
305                 310                 315                 320

Ala Ile Asp Ser Val Ile Phe Ala Thr Gly Tyr Asp Tyr Ser Tyr Pro
                325                 330                 335

Phe Leu Asp Glu Thr Ile Met Lys Ser Arg Asn Asn Glu Val Thr Leu
            340                 345                 350

Phe Lys Gly Ile Phe Pro Pro Leu Met Glu Lys Pro Thr Leu Ala Val
        355                 360                 365

Ile Gly Leu Val Gln Ser Leu Gly Ala Ala Ile Pro Thr Ala Asp Leu
```

```
                370              375              380
Gln Ala Trp Trp Ala Ala Lys Val Phe Ala Asn Ser Cys Thr Leu Pro
385              390              395              400

Thr Thr Asn Glu Met Met Asp Asp Thr Asp Glu Lys Met Gly Lys Lys
                405              410              415

Leu Lys Trp Phe Gly Gln Ser Gln Thr Leu Gln Thr Asp Tyr Ile Thr
                420              425              430

Tyr Val Asp Glu Leu Gly Ser Phe Ile Gly Ala Lys Pro Asn Ile Pro
                435              440              445

Trp Leu Phe Leu Thr Asp Pro Arg Leu Ala Leu Glu Val Tyr Phe Gly
                450              455              460

Pro Cys Ser Pro Tyr Gln Phe Arg Leu Met Gly Pro Gly Lys Trp Asp
465              470              475              480

Gly Ala Arg Asn Ala Ile Leu Thr Gln Trp Asn Arg Thr Val Lys Pro
                485              490              495

Thr Arg Thr Arg Val Val Ser Glu Val Gln Arg Pro His Pro Phe Tyr
                500              505              510

Asn Leu Leu Lys Met Leu Ser Phe Pro Leu Leu Leu Ala Val Thr
                515              520              525

Leu Thr Phe Tyr
    530

<210> SEQ ID NO 7
<211> LENGTH: 21
<212> TYPE: DNA
<213> ORGANISM: Artificial Sequence
<220> FEATURE:
<223> OTHER INFORMATION: oligonucleotide

<400> SEQUENCE: 7
tcacatagag tgctatgggg g                                        21

<210> SEQ ID NO 8
<211> LENGTH: 25
<212> TYPE: DNA
<213> ORGANISM: Artificial Sequence
<220> FEATURE:
<223> OTHER INFORMATION: oligonucleotide

<400> SEQUENCE: 8
cttaggaaga agataaaaat gcaac                                    25

<210> SEQ ID NO 9
<211> LENGTH: 23
<212> TYPE: DNA
<213> ORGANISM: Artificial Sequence
<220> FEATURE:
<223> OTHER INFORMATION: oligonucleotide

<400> SEQUENCE: 9
aatgtccatc atcatagttc tct                                      23

<210> SEQ ID NO 10
<211> LENGTH: 23
<212> TYPE: DNA
<213> ORGANISM: Artificial Sequence
<220> FEATURE:
<223> OTHER INFORMATION: oligonucleotide

<400> SEQUENCE: 10
taggcttgtg tagcctgccc tca                                      23
```

```
<210> SEQ ID NO 11
<211> LENGTH: 16
<212> TYPE: DNA
<213> ORGANISM: Artificial Sequence
<220> FEATURE:
<223> OTHER INFORMATION: oligonucleotide

<400> SEQUENCE: 11
cctcagagag aactat                                                       16

<210> SEQ ID NO 12
<211> LENGTH: 16
<212> TYPE: DNA
<213> ORGANISM: Artificial Sequence
<220> FEATURE:
<223> OTHER INFORMATION: oligonucleotide

<400> SEQUENCE: 12
ggagtctctc ttgata                                                       16

<210> SEQ ID NO 13
<211> LENGTH: 16
<212> TYPE: DNA
<213> ORGANISM: Artificial Sequence
<220> FEATURE:
<223> OTHER INFORMATION: oligonucleotide

<400> SEQUENCE: 13
cctcaaagag aactat                                                       16

<210> SEQ ID NO 14
<211> LENGTH: 16
<212> TYPE: DNA
<213> ORGANISM: Artificial Sequence
<220> FEATURE:
<223> OTHER INFORMATION: oligonucleotide

<400> SEQUENCE: 14
ggagtttctc ttgata                                                       16
```

NUCLEOTIDE SEQUENCE WHICH ENCODES A FLAVIN MONOOXYGENASE, THE CORRESPONDING PROTEIN AND THEIR USES IN THE SPHERES OF DIAGNOSIS AND THERAPY

RELATED APPLICATIONS

The present application is a continuation of PCT application Ser. No. PCT/FR/97/02226, filed Dec. 5, 1997 (the disclosure of which is incorporated herein in its entirety) which claims priority from French Patent Application Serial Number 96/15032, filed Dec. 6, 1996, the disclosure of which is incorporated herein by reference in its entirety.

The present invention relates, in particular, to human flavin monooxygenase 2 (hFMO2), as well as to another human enzyme of the FMO family, i.e. hFMOx, and to their nucleotide and polypeptide sequences. The present invention also relates to cloning and/or expression vectors which contain said nucleotide sequences and to cells which are transformed with these vectors, as well as to methods for preparing said polypeptides. The invention also encompasses methods for selecting compounds and for diagnosing predisposition to pathologies and/or deficiencies which are linked to the FMOs as well as to pharmaceutical compositions which comprise said compounds, which are intended for treating and/or preventing these pathologies.

The flavin monooxygenases (FMOs) (Lawton et al., 1994) form a family of microsomal enzymes which catalyze the NADPH-dependent oxidation of a large number of exogenous organic compounds (xenobiotics) which possess a nucleophilic heteroatom such as, in particular, the nitrogen, the sulfur, the phosphorus or the selenium atom (Ziegler D. M., 1988; Ziegler D. M., 1993), whether the xenobiotics are drugs, pesticides or other potentially toxic substances. Cysteamine is currently the only known endogenous substrate of the FMOs.

The FMOs represent a multigenic family. Expression of different forms of FMO depends both on the tissue and the species under consideration.

FMOs have been located in various types of tissue, in particular the liver, the lungs and the kidneys.

To date, five isoforms of FMO have been characterized in the reference species, which is the rabbit. Their homology is 50–60%. Four of these isoforms, i.e. FMO1, FMO3, FMO4 and FMO5, have been identified in humans (GeneBank sequences M64082, M83772, Z11737 and L37080, respectively). Among the mammalian species, the homology between orthologous FMOs is greater than 80%. It is reasonable to postulate that an FMO2, if not to say other isoforms, exist(s) in humans.

The FMOs are associated with the endoplasmic reticulum and are involved in detoxifying xenobiotic compounds, with monooxygenation enabling the xenobiotic to be transformed into a more polar substance, with this transformation being the preliminary step prior to its excretion. The FMOs may also be involved in the metabolic activation of various toxic and/or carcinogenic compounds which are present in the environment.

The mechanism of the FMO reaction has been described in detail (Poulsen, L. L. et al., 1995). In contrast to all the other known oxidases or monooxygenases, the FMOs possess the unique property of forming a stable, NADP(H)- and oxygen-dependent enzyme intermediate, i.e. 4α-hydroperoxyflavin, in the absence of oxidizable substrate. Because the catalytic energy is already present in the FMO enzyme before contact with its potential substrate, the appropriateness of the substrate does not have to be as precise as in the case of other types of enzyme. This specific characteristic of FMO is responsible for the large variety of substrates which are accepted by the FMOs (including, for example, tertiary and secondary alkylamines and arylamines, many hydrazines, thiocarbamides, thioamides, sulfides, disulfides and thiols).

Many molecules which are active compounds of drugs are recognized as being substrates of the FMOs, either for an N oxidation or for an S oxidation (Gasser, 1996), with these molecules including, in particular, antidepressants, neuroleptics, anti-ulcer drugs, vasodilators and antihypertensives.

Although some FMO substrates are oxidized into less active derivatives, a large number of nucleophilic compounds can be metabolized into intermediates which may be more reactive and/or potentially toxic; rather than being excreted, such products may induce toxic responses by means of covalent binding to cell macromolecules, or by means of other mechanisms. For example, mercaptopyrimidines and thiocarbamides may be mainly activated by FMO activity (Hines et al., 1994). More precisely, it has been demonstrated that the nephrotoxicity which is associated with the glutathione conjugate of acrolein is linked to its metabolism mediated by renal FMO; the FMO forms an S-oxide which is then released, by an elimination reaction which is catalyzed in basic medium, in the form of cytotoxic acrolein (Park, S. B. et al., 1992). Thus, the FMOs can play an important role both in the first steps of chemical toxicity and in the detoxification of xenobiotic compounds.

As described above, a large number of drugs which are currently at the clinical trial stage, or else widely prescribed, contain nucleophilic functions of the nitrogen, sulfur, phosphorus or other type. However, the role of FMO in the oxidative metabolism of drugs and endogenous chemical compounds in humans is not well understood.

Cashman et al. (1996) have recently studied the contributions of the FMO enzymes in the physiological metabolism of cimetidine and S-nicotine in vivo. The greater part of their results confirms the fact that the FMO3 activity of the adult liver is responsible for the oxygenation of cimetidine and S-nicotine, with this oxygenation being stereospecific. The authors furthermore demonstrate that the stereochemistry of the main metabolites of cimetidine and S-nicotine in small experimental animals is different from that observed in humans and suggest that different FMO isoforms may predominate depending on the species, with this possibly having important consequences with regard to the choice of experimental animals for programmes for elaborating and developing drugs for humans.

FMO1 is known to be expressed in humans in the kidneys but not in the liver. FMO2 is expressed in the main in the lungs in all the mammalian species tested. In humans, FMO3 was isolated from the liver, where it predominates in adults. FMO3 is the main isoform involved in the sulfoxidation of methionine and in the stereospecific oxygenation of cimetidine and S-nicotine. FMC3 exhibits a greater specificity for its substrate than that exhibited by the FMO1 enzymes which are found in the livers of most animal species studied. FMO4 is a minor isoform whose function and substrate specificity are not well known. It is present in the human liver and is also expressed in the brain, where it could be involved in the oxidation of antidepressant drugs such as imipramine. FMO5 is expressed in the human liver to a lower extent than is FMC3. Its apparent lack of efficacy as an enzyme involved in the metabolism of drugs suggests that it could be involved in a physiological function.

The differing expression profiles of the FMO isoforms, depending on tissues and/or species, therefore probably constitute a significant factor contributing to the differences in FMO activity which are observed between tissues and/or between species. Thus, the variety of FMO forms could have a significant impact on the differences in the responses of tissues and/or species to exposure to a xenobiotic compound. This is because the differences which are observed between tissues and/or species in the response to xenobiotic compounds, and in the toxicity of these compounds, are linked, to a substantial extent, to variations in the activity and specificity involved in the metabolism of these substrates by the FMOs. Genetic factors and tissue specificity in the expression of the FMOs are important factors in these variations.

With regard to genetic factors, it has been reported, for example, that trimethylaminuria, which is a condition which is present in 1% of white British subjects and which is expressed in a strong odor of rotting fish in the expired air, the sweat or the urine, is linked to a deficiency of genetic origin in the functioning of an hepatic FMO.

For the reasons which have previously been mentioned, there therefore currently exists a considerable need to identify new isoforms of FMO, as well as the genetic polymorphisms which may be associated with them, which exhibit specificities with regard to their substrates and/or their tissue expression profile, which could be involved in the metabolism of xenobiotics, such as the metabolism of drugs or of exogenous substances which are present in the environment, such as, for example, pesticides, or else which could be involved in a physiological function. This is precisely the object of the present invention.

Figure 1:
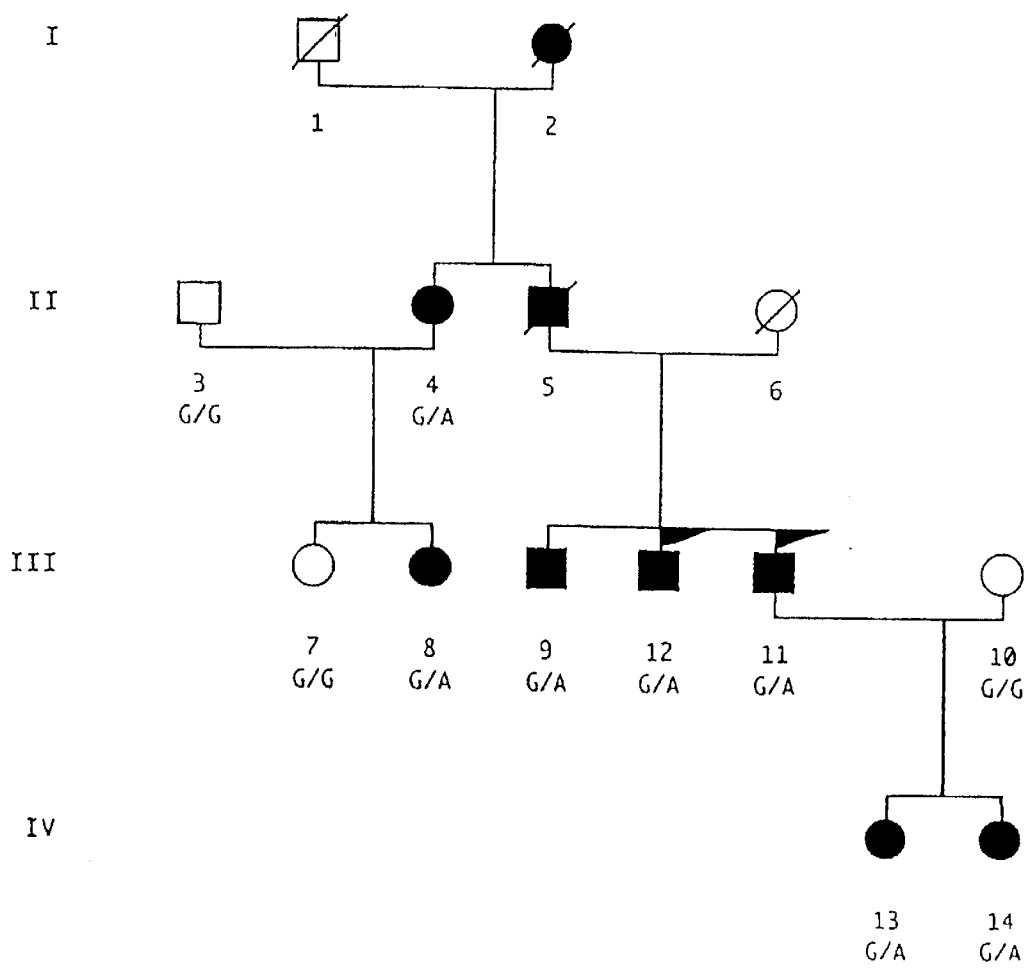
FIG. 1: Analysis of the segregation of the G.1263mac.A polymorphism in the family studied.

The genomic DNA of individuals 3, 4 and 7 to 14 was amplified by PCR and the sequences of the resulting fragments were analyzed in order to detect heterozygosity sites which segregated with the disease.

The filled-in symbols indicate the individuals suffering from juvenile POAG. The barred symbols indicate individuals who were not genotyped. Individuals 11 and 12 are twins.

G/G=homozygotes for the base in the position which is homologous to position 1263 of the macaque FMO2 mRNA.

G/A=heterozygotes for the base which is in the position which is homologous to position 1263 of the macaque FMO2 mRNA.

BRIEF DESCRIPTION OF THE TABLES

Table 1 depicts primer sequences which can be use for amplifying the sequences which are of interest in relation to the G.1263mac.A. mutation.

Table 2 lists examples of primers which can be used for detecting the G.1263mac.A mutation by Single nucleotide primer extension.

Table 3: Example of a restriction enzyme which can be used for detecting the G.1263mac.A mutation by Restriction Fragment Length Polymorphism (RFLP).

Table 4: Examples of probes which can be used for detecting the G.1263mac.A mutation by allele specific oligonucleotide (ASO).

Table 7A: Description of the exon/intron structure of the gene which encodes hFMO2, which is the human homologue of macaque FMO2. The positions where the exons begin and end are shown on the nucleotide sequences SEQ ID No. 1 and No. 2.

Table 7B: Description of the exon/intron structure of the gene encoding hFMOx. The positions where the exons begin and end are shown on the nucleotide sequences SEQ ID No. 4 and No. 5.

Table 8: Homology between the macaque FMO2 gene and its human homologue. The 5' untranslated region diverges slightly from the macaque sequence.

Table 9: Summary of the positions at which the human hFMO2 mRNA sequence varies as compared with the homologous macaque sequence; influence of the variations on the protein sequence.

Several genes of the human FMO family have been located on the 1q23-25 region of chromosome 1 by means of in situ hybridization of the metaphase chromosome.

Once such a candidate region has been defined, it is necessary to have access to the fragment of the genome which covers the distance over which the sought-after gene(s) is/are located. This step proceeds through the drawing up of a physical map, namely the covering of the region with a set of cloned and ordered fragments. At present, thanks to the data of the CEPH/Généthon integrated map of the human genome, approximately 80% of the genome is covered by YAC clones which are subcloned into BACs whose location on the chromosomes is determined by means of polymorphic and genetically ordered markers (Chumakov et al., 1995). This physicogenetic map makes it possible to save a considerable amount of time, in particular by the use of exhaustive sequencing of the regions of interest.

Thus, according to the present invention, it was established, after locating the BAC 123H04M on the previously mentioned genetic locus 1q24-25, that the insert which it carries contains the 3' part of hFMO3 and the 5' part of hFMO1 as well as the complete sequence of hFMO2 and that of another new gene which is a member of the FMO family, i.e. hFMOx.

Furthermore, as a result of using 5' label libraries, it is possible to verify the expression of the candidate genes which have been identified as above: the identification of a label which hybridizes to one of the candidate sequences indicates, since this sequence is derived from a cDNA library, the presence of mRNA and therefore of expression of the sequences in question in the tissues under consideration.

For this reason, the present invention relates, in particular, to an isolated polynucleotide whose sequence, i.e. SEQ ID No. 1, which encodes a polypeptide having the sequence SEQ ID No. 3.

The present invention also relates to an isolated polynucleotide whose sequence, i.e. SEQ ID No. 4, which encodes a polypeptide having the sequence SEQ ID No. 6.

These two nucleotide sequences are those of two genes which encode novel enzymes of the human flavin monooxygenase (FMO) family, i.e. hFMO2 and hFMOx, respectively. This was established by comparing the identified sequences with the previously known FMO sequences: the conclusion was made possible by very strong structural homologies between the two sequences studied and those of the FMOs, very strong homologies between the first sequence and the known FMO2s, in particular the macaque FMO2 (macaque FMO2: GeneBank sequence U59453), as well as insufficient homology of the second sequence with any of the FMOs which have already been itemized in humans.

The exon structure of the already known genes of the FMO family is entirely conserved in the hFMO2 nucleotide sequence according to the invention. The sequences of each of the 9 exons of the polynucleotide according to the invention (Table 7) exhibit degrees of DNA homology varying from 95% to 98% with the corresponding sequence of the messenger RNA of the macaque FMO2 (Talbe 8). The divergences between the two nucleotide sequences, as well as their significance for the peptide sequence, are shown in Table 9. The polynucleotide sequence SEQ ID No. 1 according to the invention encodes a polypeptide of 535 amino acids having the sequence SEQ ID No. 3; the sequence SEQ ID No. 2 of the predicted messenger RNA, as well as the polypeptide sequence of the human protein, are 97% homologous with those of the macaque FMO2, thereby making it possible to identify the polypeptide according to the invention as being human FMO2. The polypeptide having the sequence SEQ ID No. 3, also exhibits a high degree of homology with other mammalian flavin monooxygenases 2; its degrees of homology with other proteins of the flavin monooxygenase family are lower.

As previously mentioned, the lack of sufficient homology between the sequences corresponding to hFMOx—genomic (SEQ ID No. 4), messenger RNA (SEQ ID No. 5) and peptide (SEQ ID No. 6) sequences—and the sequences of the known FMOs enabled the conclusion to be drawn that hFMOx is a novel FMO isoform.

The present invention therefore relates to the DNA or RNA sequences, with the DNA being able to be genomic DNA, complementary DNA or synthetic DNA, of the FMOs, in particular of hFMO2 and hFMOx, as well as to the corresponding proteins.

The present invention furthermore relates to cloning and/or expression vectors which contain said nucleotide sequences, to cells which are transformed with these vectors or to animals which contain said cells, as well as to methods for preparing said polypeptides in the form of recombinant polypeptides.

The invention also encompasses methods for selecting a compound which is able to modulate FMO activity.

The invention also relates to methods for diagnosing predisposition to FMO-linked disorders as well as to pharmaceutical compositions which are intended for treating and/or preventing these disorders.

A first example of such disorders could be primary open-angle glaucoma (POAG). Thus, on the one hand, Sunden et al., (1996), as well as the inventors (Belmouden et al., 1996), have identified the chromosomal region GLC1A, which carries, among other gene sequences, those known sequences of the FMO family, in 1q23-25, as being linked to the appearance of juvenile POAG (J-POAG). On the other hand, a possible role for monooxygenases in the etiology of glaucoma has previously been suggested (Schwartzman et al., 1987). Thus, it has been suggested that, by inhibiting the Na+, K+, ATPase activity in the cornea, oxidation reaction metabolites might contribute to regulating the transparency of the cornea and ocular humoral secretion; it should be noted that opacity of the cornea and ocular hypertension are the two main criteria for diagnosing glaucoma.

Thus, the inventors have identified a site of heterozygosity, exhibiting genotypic segregation in a family studied for the presence within it of a large number of members suffering from J-POAG, in exon 8 of the hFMO2 polypeptide according to the invention.

By looking for polymorphisms which are present in appropriately selected populations and which are located in sequences which correspond to those carried by the BAC 123H04M insert, or more generally by the FMO sequences, it will be possible to identify, in particular, the mutations which are associated with pathologies or disorders which are linked to an alteration in the FMOs.

The various FMO isoforms appear to differ from each other less by the tissue specificity of their expression than by the substrates whose transformation they catalyze. As previously pointed out, FMOs have been shown to be expressed in the liver, the lungs, the kidneys and the brain.

The pathogenic effect of a functional deficit in an FMO could result in a decreased capacity of the tissues, in which it is expressed, to resist oxidative stress.

More generally, as a result of their role in oxidative metabolism and their detoxification function, the FMOs could be involved in any degenerative or toxic pathology which has been demonstrated or is still to be proved, in particular those pathologies in which programmed cell death has been shown to take place, and the degenerative diseases of the central nervous system.

In a general manner, the pathologies linked to FMO function are grouped under the name "FMO-linked disorders".

FMO-linked disorders which may be mentioned by way of example, but without any limitation to these disorders, are:

oxidation of drugs, which are FMO substrates, to form less active derivatives, implying a loss of efficacy of said drug;

failure to metabolize drugs which are active in metabolite form; loss of efficacy of said drug;

failure to metabolize toxic and/or carcinogenic xenobiotics, including exogenous substances which are naturally present in the diet, such as plant alkaloids, or toxic substances which are present in the environment, such as pesticides or herbicides;

metabolism of drugs to form intermediates which may be more reactive, implying overdosing with the possibility of side-effects;

metabolism of xenobiotics, including drugs or other exogenous substances, to form intermediates which may potentially be toxic; and/or alteration of the physiological function in which the FMO is involved; in particular alteration of FMO function could be involved in the symptomatology of glaucoma.

"FMO" will be understood as referring to any human FMOs which are known, i.e. FMO1, FMO3, FMO4 and FMO5, or which are newly described in the present patent application, namely FMO2 or FMOx.

While some of these disorders may have a multigenic origin, it applies to all of them that alterations to one or more FMOs contribute to the appearance of the disorder or to its aggravation.

The Nucleotide Sequences

The present invention first of all relates to an isolated nucleotide sequence which is distinguished in that it is selected from:

a) the sequences which encode the human FMO2 or FMOx proteins and their protein variants, b) the sequences which encode a fragment of these proteins which possesses at least 10 bases, c) the human FMO2 or FMOX genomic sequences and their alleles, d) the sequences which exhibit at least 80%, preferably at least 90%, homology with the sequences (a) and (c), e) the fragments of the sequences (c) or (d) which possess at least 10 bases, f) the sequences which hybridize with a sequence from (a) to (e).

It should be understood that the present invention does not relate to the genomic nucleotide sequences in their natural chromosomal environment, that is to say in their natural state; the present invention relates to sequences which have been isolated, that is which have been picked out directly or indirectly, for example by making a copy (cDNA), with their environment having been at least partially modified.

Thus the sequences to which the invention relates can just as well be cDNA as genomic DNA which is partially modified or carried by sequences which are at least partially different from the sequences which carry them naturally.

These sequences can also be described as being "unnatural".

A "nucleic acid sequence" is understood as being a natural, isolated, or synthetic, DNA and/or RNA fragment which designates a precise sequence of modified or unmodified nucleotides, which sequence makes it possible to define a fragment, a segment or a region of a nucleic acid.

"Alleles" are understood as referring to the mutated natural sequences which correspond to polymorphisms which may exist in the human being, in particular those which may lead to the development of FMO-linked disorders.

"Protein variant" is understood as referring to the entirety of the mutated proteins which may exist in the human being and which correspond, in particular, to truncations, substitutions, deletions and/or additions of amino acid residues, as well as the artificial variants which will nevertheless also be termed "protein variants". In the present case, the variants are linked in part to the occurrence of FMO-linked disorders.

According to the invention, the fragments of nucleic acid sequences may, in particular, encode domains of the protein or else be used as probes or as primers in detection, identification or amplification methods. These fragments are at least 10 bases in size, and preference will be given to fragments which contain 20 bases, preferably 30 bases.

According to the invention, the homology is solely of the statistical type; it signifies that the sequences possess at least 80%, preferably 90%, of their nucleotides in common.

As far as the (f) sequences are concerned, the hybridization conditions should ensure, according to the invention, at least 95% homology.

More specifically, the present invention relates to a nucleotide sequence which is selected from:

a) the sequences which encode a polypeptide which comprises the amino acids according to the sequence SEQ ID No. 3 or according to the sequence SEQ ID No. 6, b) the nucleic acid sequences of SEQ ID No. 1 or No. 2, or the nucleic acid sequences of SEQ ID No. 4 or No. 5, or the nucleic acid sequences which encode the corresponding polypeptides, c) a fragment of a sequence according to (a) or (b) which contains at least 10 bases, and d) a sequence which contains at least one point mutation as compared with the sequences (a), (b) or (c), e) a sequence which is complementary to the sequences (a), (b), (c) or (d).

The structure of the hFMO2 gene is identified in Table 7A.

The previous comments apply as far as the specific comments on (a), (b), (c), (d) and (e) are concerned.

The invention also relates to fragments of these sequences, in particular sequences which encode polypeptides which have retained all or part of the activity of the FMO protein.

Some of these sequences may be identified by referring, in particular, to Table 7A, which provides an overview of the organization of hFMO2.

These partial sequences can be used for a large number of applications, as will be described below, in particular for making protein constructs of the FMO type or of different types, but also for producing, for example, FMO-like proteins.

Even if the sequences described are in general the normal sequences, the invention also relates to sequences which are mutated to the extent that they contain at least one point mutation, preferably mutations extending to no more than 10% of the molecule.

Preferably, the present invention relates to mutated nucleotide sequences in which the point mutations are not silent, that is to say they lead to a change in the encoded amino acid as compared with the normal sequence. Still more preferably, these mutations concern amino acids which form the structure of the FMO proteins or the corresponding fragments of these proteins, in particular in the regions corresponding to the catalytic sites, to the regulatory sites or to the sites for binding cofactors; the mutations may also concern the sequences which are involved in transport and targeting; they may also, in particular, delete cysteines or, on the contrary, make them appear, but also change the character of the protein either with regard to charge or with regard to hydrophobicity.

The present invention also relates to the mutations which may occur in the promoter and/or regulatory sequences of the human FMO genes, which mutations may exert effects on the expression of the protein, in particular on the level at which it is expressed.

In a general manner, the present invention is concerned with both normal FMO proteins and mutated FMO proteins as well as their fragments and the corresponding DNA and RNA sequences.

Among the nucleotide fragments which may be of interest, in particular for diagnosis, mention should also be made of the genomic intron sequences of the FMO gene, for example the junction sequences between the introns and the exons.

The invention encompasses the nucleotide sequences according to the invention which are distinguished in that they comprise at least the mutation G.1263mac.A, as will be defined below in the examples.

The invention also encompasses the nucleotide sequences according to the invention which are distinguished in that they contain at least 10 bases, as well as said nucleotide sequences, which can be used, in particular, as primers which are specific for an allele.

The invention also encompasses the nucleotide sequences according to the invention which can be used, in particular, as nucleic acid primers, which are preferably distinguished in that said sequences are selected from the sequences SEQ ID No. 7, SEQ ID No. 8, SEQ ID No. 9 and SEQ ID No. 10.

The invention furthermore relates to the nucleotide sequences according to the invention which can be used, in particular, as probes which are specific for an allele and which are preferably distinguished in that said sequences are selected from the sequences SEQ ID No. 11, SEQ ID No. 12, SEQ ID No. 13 and SEQ ID No. 14.

The invention also relates to the nucleotide sequences according to the invention which are distinguished in that said sequences encode one of the FMO domains.

The polypeptides which are encoded by the nucleotide sequences according to the invention, in particular the polypeptides having the sequence SEQ ID No. 3 or SEQ ID No. 6, naturally also belong to the invention.

In the present description, the terms protein, polypeptide or peptide are interchangeable.

The present invention relates to all the primers which can be deduced from the preceding nucleotide sequences and which can enable these sequences to be detected by using an amplification method such as the PCR method.

The present invention also relates to the nucleotide sequences which can contain unnatural nucleotides, in particular sulfur-containing nucleotides or nucleotides having an $\alpha$ or $\beta$ structure.

Finally, the present invention naturally relates to both DNA and RNA sequences as well as to the sequences which hybridize with them and to the corresponding double-stranded DNA molecules.

Nucleic acid fragments of interest which should in particular be mentioned are anti-sense oligonucleotides, that is to say oligonucleotides whose structure ensures, by hybridization with the target sequence, that expression of the corresponding product is inhibited. It is also necessary to mention sense oligonucleotides which, by interacting with proteins which are involved in regulating expression of the corresponding product, induce either an inhibition or an activation of this expression.

As will be described below, it may be necessary, for some applications, to envisage mixed, protein/DNA/chemical compound, constructs, in particular the use of intercalating agents, for example; it should be understood that such compounds are covered by the patent as containing a sequence according to the invention.

The Proteins and Polypeptides

The present invention also relates to the proteins, polypeptides or peptides which correspond to the previously mentioned sequences and which are in unnatural form, that is to say that they are not used in their natural environment but that they were obtained by purification from natural sources or else obtained by genetic recombination, as will be described below.

The invention also relates to the same polypeptides or proteins which are obtained by chemical synthesis and which can contain unnatural amino acids.

The present invention relates to recombinant proteins which are thus obtained both in glycosylated form and in unglycosylated form and which may or may not possess the natural tertiary structure.

The Vectors and the Cells

The present invention also relates to cloning and/or expression vectors which contain a nucleotide sequence as described above.

These cloning and expression vectors can contain elements which ensure expression of the sequence in a host cell, in particular promoter sequences and regulatory sequences which are effective in said cell.

The vector in question can be an autonomously replicating vector or else a vector which is intended to ensure that the sequence is integrated into the chromosomes of the host cell.

In the case of autonomously replicating systems, which are prokaryotic or eukaryotic depending on the host cell, use is preferably made of plasmid systems or viral systems, with the viral vectors being able, in particular, to be adenoviruses (Perricaudet et al., 1992), retroviruses, poxviruses or herpesviruses (Epstein et al., 1992). The skilled person is acquainted with the technologies which can be used for each of these viruses.

Thus, it is known to use, as viral vectors, defective viruses which are cultured in complementing cells, thereby avoiding the possible risk of an infectious viral vector proliferating.

When it is desired to integrate the sequence into the chromosomes of the host cell, it is necessary to arrange for one or more sequences derived from the host cell to be integrated at each end of the nucleotide sequence in order to ensure that recombination takes place. The methods used in this case are also widely described in the prior art. Use can, for example, be made of plasmid or viral systems; examples of these viruses are retroviruses (Temin 1986) or AAVs, i.e. adenovirus associated viruses (Carter 1993).

The invention also relates to the prokaryotic or eukaryotic cells which are transformed with an above-described vector, with this transformation being to ensure expression of a natural or variant FMO protein or else, for example, one of its domains.

The animals which are distinguished in that they contain a transformed cell according to the invention also belong to the invention.

The invention furthermore encompasses a method for producing a polypeptide according to the invention, which method is distinguished in that a cell according to the invention is cultured and in that the protein which is produced is recovered.

As has been previously pointed out, the present invention also relates to the polypeptides which are obtained by culturing the cells which have been transformed in this way and recovering the polypeptide which is expressed, with it being possible to effect said recovery intracellularly or else extracellularly in the culture medium when the vector has been designed for ensuring the secretion of the polypeptide by means, for example, of a leader sequence, with the protein being expressed in the form of a preprotein or a preproprotein. The constructs which permit secretion of the polypeptides are known, both for prokaryotic systems and for eukaryotic systems. Within the context of the present invention, some of the FMO polypeptides may contain their own system for secretion or membrane insertion.

Preferably, the invention relates to the polypeptides which are specific for mutated forms of the proteins according to the invention, distinguished in that their sequences are selected from the polypeptide sequences which contain at least one mutation.

Cells which can be used for producing these polypeptides and which should be mentioned are, of course, bacterial cells (Olins and Lee, 1993), but also yeast cells (Buckholz, 1993), as well as animal cells, in particular cultures of mammalian cells (Edwards and Aruffo, 1993), but also insect cells in which it is possible to use methods employing baculoviruses, for example (Luckow, 1993).

The cells which are thus obtained can be used to prepare both natural or variant FMO polypeptides and also fragments of these polypeptides, in particular polypeptides which correspond to the different domains in question.

The invention also encompasses the monoclonal or polyclonal antibodies which are preferably directed against the polypeptides according to the invention, which antibodies are distinguished in that they are obtained by the immunological reaction of a human or animal organism with an immunogenic agent consisting of a polypeptide according to the invention, in particular a recombinant or synthetic polypeptide according to the invention; preferably, the immunogenic agent will consist of a polypeptide which is specific for the mutated form of the protein which is obtained in accordance with the previously described method, with the sequence of said polypeptide being selected from the polypeptide sequences which contain at least one mutation.

The invention also relates to the antibodies according to the invention, which are distinguished in that they are labeled antibodies, in particular for imagery.

These monoclonal or polyclonal antibodies, which are labeled and which correspond, in particular, to all or part of the mutated proteins, can be used, for example, in vivo or ex vivo as imagery agents on biological samples (imagery using antibodies which are coupled to a molecule which is detectable in imagery of the PET-scan type, for example).

The Cell Models

The transformed cells, as described above, can also be used as models in order to study the interactions between the FMOs and their partners, i.e. chemical and protein compounds which are directly or indirectly involved in FMO activity, and in order to study the different interactions which are involved depending on whether the FMO is a normal FMO or a variant FMO. However, in particular, they can be used for selecting products which interact with the normal or variant FMOs as agonists, in particular enzyme activators, or antagonists, in particular enzyme inhibitors.

Another potential application of the characterization of these genes is therefore the possibility of identifying compounds, in particular protein compounds, which interact with these FMOs. These compounds can be either inhibitors or activators, for example substrates or cofactors. Their identification makes it possible to use them in accordance with their interactions with the normal protein or the variant protein. In particular, it is possible to seek to isolate agents which have different effects on the normal FMOs and the variant FMOs.

It is also possible to use these cell models for studying the metabolism of xenobiotics, drugs or other compounds by a normal or variant FMO. This can be done in association with identifying the toxic potency of particular compounds, in association with selecting and developing compounds having reduced toxicity or having increased activity or in association with selecting and developing modified FMOs which have an increased ability to metabolize the compounds of interest.

This type of cell model can be constructed using genetic engineering techniques. Depending on the type of cell which it is desired to use, it is a matter of cloning the gene in question, in its normal form or in its mutated form, into an expression vector, whether it be an autonomously replicating vector or an integrating vector, with said vector containing all the elements for expressing the gene in the cell in question, or with the latter possessing all the elements for expressing the sequence in question.

This thereby results in eukaryotic or prokaryotic cells which are expressing the normal or variant FMO protein(s) and which can then constitute models for testing, at the same time, the interactions of different products with the FMO proteins or their variants or for testing compounds, in particular synthetic chemical products, which can interact with the product of the normal or mutated FMO gene, with these compounds being added to the culture medium of said cells.

It should, in particular, be noted that the products in question can equally well be agents having an antagonistic activity as agents having an agonist activity.

The use of cell models for the purpose of testing pharmaceutical compounds is well known, and once again there is no need to describe this type of model in detail. However, of the techniques employed, those which may be mentioned are phage display (Allen et al., 1995) and the two-hybrid methods (Luban and Goff., 1995).

These models can be of the in vitro type, for example cultures of human cells, either in normal culture or, possibly, in the form of an isolated organ.

The present invention also relates to organisms such as animals, in particular mice, which are expressing the phenotype corresponding to the normal or variant FMO of human origin. In this case too, these animals can be used as model animals for testing the efficacy of particular pharmaceutical products.

The present invention also relates to the products which are obtained by using the above-described cell models.

Diagnostic Method

As has previously been mentioned, the present invention relates, more particularly, to methods for diagnosing predisposition to FMO-linked disorders in a patient, which methods are distinguished in that a biological sample taken from said patient is used for determining the presence of a mutation in at least one sequence encoding an FMO by means of analyzing all or part of a nucleic acid sequence corresponding to said gene, with the presence of at least one such mutation being indicative of a predisposition of said patient to FMO-linked disorders.

It is important to make clear that, while the present invention only describes hFMO2 and hFMOx in detail, the diagnostic methods and the compositions for therapeutic purposes relate both to the abovementioned FMOs and to FMO1, FMO3, FMO4 and FMO5. This is because the FMOs, in general, are involved in the metabolism of xenobiotics and the disorders which are associated with them, such as, for example, the xenobiotics and the FMO-linked disorders which have been mentioned above.

The mutation, of those which have been investigated, which should be mentioned more specifically is the G.1263mac.A. mutation.

The analyzed nucleic acid sequences can equally well be genomic DNA, a cDNA or an MRNA.

While, as has previously been mentioned, the FMO-linked disorders which can be detected are more specifically understood as being the pathologies which are associated with xenobiotic metabolism, as mentioned above, or which are associated with the biological function of FMO, other disorders which could be linked to an FMO anomaly may also exist.

Although the diagnostic tools which are based on the present invention can make it possible to achieve a positive and differential diagnosis in a patient taken in isolation, they are preferably of value for achieving a presymptomatic diagnosis in a patient who is at risk, in particular with a familial case history, and it is also possible to envisage an antenatal diagnosis.

Furthermore, the detection of a specific mutation may enable a prognostic diagnosis to be made, in particular with regard to the intensity of the disorder or the probable time at which it will appear.

Of course, there are a very large number of methods for detecting the mutation in a gene as compared with the natural gene. These methods may essentially be divided into two broad categories; the first type of method is that in which the presence of a mutation is detected by comparing the mutated sequence with the corresponding natural, unmutated sequence, and the second type is that in which the presence of the mutation is detected indirectly, for example by detecting mispairings which are due to the presence of the mutation.

In the two cases, preference is given, in general, to the methods in which all or part of the sequence corresponding to an FMO is amplified prior to detecting the mutation, with these amplification methods being effected by means of so-called PCR or PCR-like methods. PCR-like is to be understood as referring to all the methods which employ direct or indirect reproductions of the nucleic acid sequences or else in which the labelling systems have been amplified; these techniques are, of course, well known; in general, they involve amplification of the DNA with a polymerase; when the original sample is an RNA, it is advisable first of all to carry out a reverse transcription. There are currently a very large number of methods for achieving this amplification, for example the methods termed NASBA "nucleic acid sequence based amplification" (Compton 1991), TAS "transcription based amplification system" (Guatelli et al., 1990), LCR "ligase chain reaction" (Landegren et al., 1988), "endo run amplification" (ERA), "cycling probe reaction" (CPR) and SDA "strand displacement amplification" (Walker et al., 1992), which methods are well known to the skilled person.

Table 1 depicts primer sequences which can be use for amplifying the sequences which are of interest in relation to the G.1263mac.A. mutation.

The reagent employed for detecting and/or identifying a mutation of the FMO gene in a biological sample comprises a so-called capture probe and/or a so-called detection probe, with at least one of these probes containing a previously described sequence according to the present invention.

Search for Point Mutations

In a general manner, several detection methods can be implemented, or adapted if necessary, after the sequences of interest have been amplified by PCR. The following may be mentioned by way of example:

1) Sequencing: comparing the sequences from several individuals and/or pinpointing a site of heterozygosity in a single individual.
2) "Single nucleotide primer extension" (Syvanen et al., 1990). Examples of primers which can be used for detecting the G.1263mac.A mutation by this method are given in Table 2.
3) RFLP "restriction fragment length polymorphism". An example of a restriction enzyme which can be used for detecting the G.1263mac.A mutation by RFLP is given in Table 3.
4) Searching for "single strand conformation polymorphisms" (SSCP).
5) Methods based on cleaving the mispaired regions (enzymic cleavage with S1 nuclease, chemical cleavage with different compounds such as piperidine or osmium tetroxide, etc.
6) Detecting a heteroduplex by electrophoresis.
7) Methods based on using allele-specific oligonucleotide probes in hybridization: "allele specific oligonucleotide" (ASO) (Stoneking et al., 1991). Examples of probes which can be used for detecting the G.1263mac.A mutation by ASO are given in Table 4.
8) OLA "dual color oligonucleotide ligation assay" method (Samiotaki et al., 1994).
9) ARMS "amplification refractory mutation system" method or ASA "allele specific amplification" method, or PASA "PCR amplification of specific allele" method (Wu et al., 1989).

This list is not exhaustive and other well known methods may also be used.

Searching for Alterations, for Example of the Deletion Type

Other methods which are well known and which are based on hybridization techniques using genomic probes, cDNA probes, oligonucleotide probes or riboprobes may also be used for searching for this type of alteration.

The methods, according to the invention, for diagnosing a predisposition to FMO-linked disorders in a patient, which are distinguished in that said analysis is carried out by hybridization, with said hybridization preferably being performed using at least one oligonucleotide probe which is specific for the allele, or in that the presence of a mutation is detected by comparison with the corresponding natural, unmutated sequence, or in that said analysis is carried out by sequencing or by electrophoretic migration, more specifically by SSCP or DGGE, or in that said analysis is performed using a methodology which is aimed at detecting a truncation of the protein, therefore also form part of the invention.

The methods, according to the invention, for diagnosing a predisposition to FMO-linked disorders in a patient which are distinguished in that all or part of the nucleic acid sequence of the FMO gene is amplified prior to detecting the mutation(s), with the amplification preferably being performed by PCR or a PCR-like method, and the primers selected for performing the amplification preferably being selected from the primers according to the invention, also form part of the invention.

The reagents for detecting and/or identifying a mutation of the FMO gene in a biological sample, which reagents are distinguished in that they comprise a so-called capture probe and/or a so-called detection probe, with at least one of these probes containing a sequence according to the invention or an antibody according to the invention, also form part of the invention.

Methods which are Based on Detecting the Gene Product

The mutations of the FMO gene can be responsible for different modifications of the product of this gene, with it being possible to use these modifications for a diagnostic approach. Thus, the modifications in antigenicity can make it possible to develop specific antibodies. All these modifications can be used for the purpose of a diagnostic approach due to the existence of several well known methods, such as the RIA method or the ELISA method, which are based on using monoclonal or polyclonal antibodies which recognize the normal protein or mutated variants.

Finally, it is also possible to diagnose a predisposition to FMO-linked disorders in a patient by measuring the enzyme activity of the FMO(s) in biological samples taken from said patient. Thus, measurement of this (these) activity(ies) can indicate, when compared with an internal or external standard, a predisposition to one of the abovementioned disorders.

Therapeutic Compositions

The present invention also relates to curative or preventive therapeutic treatments of FMO-linked disorders.

Use can be made of the compounds which are directly or indirectly involved in FMO activity and which are derived from using the previously described cell models.

Use can, in particular, be made of the compounds which are able to interact, in particular as agonists or antagonists, with the normal or variant FMOs.

The present invention also relates to therapeutic compositions which comprise, as the active principle, a compound which is able to modulate FMO activity; these compounds may be compounds which have a pro-FMO activity, in particular as previously described, or compounds which have an anti-FMO activity.

In a general manner, a compound which has a "pro-FMO activity" is understood as being a compound which induces FMO activity, in contrast to an anti-FMO compound, which has a tendency to reduce FMO activity. The actual effect of these types of activities will depend on the type of enzyme, i.e. normal or pathological, which is expressed.

Preference is given to using therapeutic compositions whose activity differs toward normal FMO enzymes and variant FMO enzymes.

It is first of all possible to envisage a substitution treatment, that is to say therapeutic compositions which are distinguished in that they comprise, as the active principle, a compound having a pro-FMO activity; these compounds can, in particular, be all or part of polypeptides as have previously been described or else a vector for expressing these same polypeptides or yet again chemical or biological compounds which possess a pro-FMO activity or an FMO-like activity or which induce production of FMO.

It is also possible to use therapeutic compositions in which the active principle has an anti-FMO action, in particular an anti-FMO variant action. In this case, the treatment is a suppressive treatment. The compounds can, for example, be compounds which interact with said enzymes, in particular protein compounds, in particular anti-FMO antibodies, in particular when these antibodies recognize the variant proteins. The compounds can also be chemical products which possess an anti-FMO activity, in particular antagonists of variant FMO.

Of the large number of pharmaceutical compounds which can be used, those which should more specifically be mentioned are the anti-sense sequences which interact with the normal or mutated FMO gene, or else the sense sequences which act on the regulation of the expression of these genes, with said products being able to interact downstream of the expression products which are induced by the FMOs.

The monoclonal antibodies which inhibit the FMOs, in particular the mutated FMOs, and/or which inhibit the corresponding ligands and/or the products which are induced by FMO activity, and which can, therefore, have pro or antiactivities, should also be mentioned.

It is also possible to envisage expressing proteins, or their fragments, in vivo, in particular by means of gene therapy, using the vectors which have been previously described.

Within the context of gene therapy, it is also possible to envisage using the "naked" sequences of the previously described genes or cDNAs, with this technique having been developed, in particular, by the company Vical, which demonstrated that it was possible, under these conditions, to express the protein in particular tissues without resorting to the support of a viral vector, in particular.

Still within the context of gene therapy, it is also possible to envisage using cells which are transformed ex vivo, which cells can then be reimplanted either as such or within systems of the organoid type, as is also known in the state of the art (Danos et al., 1993). It is also possible to envisage using agents which facilitate the targeting of a defined cell type, penetration into the cells or transport toward the nucleus.

Thus, the invention also relates to a therapeutic composition which is distinguished in that it comprises, as the active principle, at least one compound which is able to modulate FMO activity, preferably FMO2 and/or FMOx activity.

The invention also encompasses a therapeutic composition which is distinguished in that it comprises, as the active principle, at least one compound which is able to interact with FMO and preferably able to interact with FMO2 and/or FMOx, or a therapeutic composition according to the invention which is distinguished in that it exhibits different activities on normal FMO and on pathological FMO.

The invention also encompasses a therapeutic composition according to the invention which is distinguished in that it comprises, as the active principle, a compound having pro-FMO activity, which compound is preferably selected from the following compounds:

a) a protein or a polypeptide according to the invention, b) an expression vector according to the invention, c) a nucleotide sequence according to the invention, distinguished in that said sequence is a sense sequence which induces FMO expression.

The invention furthermore relates to a therapeutic composition according to the invention which is distinguished in that it comprises, as the active principle, a compound having an anti-FMO activity according to the invention; the active principle is preferably selected from the following compounds:

a) an anti-FMO antibody according to the invention, b) an expression vector according to the invention, c) a nucleotide sequence according to the invention, distinguished in that said sequence is an antisense sequence which inhibits FMO expression, d) a nucleotide sequence according to the invention, distinguished in that said sequence is a sense sequence which inhibits FMO expression.

The invention also relates to a therapeutic composition according to the invention, which composition is distinguished in that the active principle is a soluble sequence which interacts with FMO.

The invention also relates to the use of an active principle, preferably at least one product according to the invention which is able to modulate or interact with FMO, FMO2 and/or FMOx, for producing a drug which is intended for treating and/or preventing disorders which are linked to FMO function.

Under another aspect, the invention relates to a method for biodegrading or biosynthesizing an organic or inorganic compound, which method is distinguished in that it employs a polypeptide or a cell according to the invention.

Thus, the polypeptides having an FMO activity according to the invention can advantageously be used for biodegrading, in accordance with the oxidation reactions as described, for example, by Ziegler (Ziegler et al., 1993), the compounds which are FMO substrates, in particular the compounds as mentioned in the present description, or be used for biosynthesizing a compound of interest from said compounds which are FMO substrates, in particular for biosynthesizing a drug, a food additive, a pesticide or a herbicide.

The methods for elaborating a compound of interest, which methods are distinguished in that they use a polypeptide or a cell according to the invention do of course form part of the invention. Thus, the polypeptides or cells according to the invention can advantageously be used in vitro for determining the potential metabolism of the compound of interest and for analyzing the metabolites which may possibly be obtained, including their toxicity and/or their activity. The results which are obtained make it possible to confirm the compound or to reformulate it such that it does or does not become an FMO substrate or such that the metabolites which are formed are different.

The products which can be obtained using said biosynthetic method also form part of the invention.

Finally, the invention encompasses the use of a polypeptide or a cell according to the invention for detoxifying a xenobiotic compound which is an FMO substrate. These xenobiotic compounds can be present in the environment, as a pesticide or a herbicide, be present naturally in plants, as particular alkaloids, or can correspond to pharmaceutical compounds.

Taking into account the homologies of the known messenger RNAs of genes of the flavin monooxygenase family, these genes share the same exon/intron structure:

exon1: untranslated, variable in size and sequence, exon2: beginning of the coding region, encodes amino acids 1–44, exon3 : amino acids 45–107, exon4 : amino acids 108–161, exon5 : amino acids 162–209, exon6 : amino acids 210–275, exon7 : amino acids 276–394, exon8 : amino acids 395–419, exon9 amino acids 420–535, end of the coding region and 3' untranslated region.

The introns vary in size and complexity. We firstly isolated the sequence of three fragments from BAC 123H04M, which fragments contain all the exons of this homologue.

Fragment 1 : containing exons 1 and 2,

Fragment 2 : containing exon 3,

Fragment 3 : containing exons 4 to 9.

The sequences of two introns were then completed and the structure is depicted in Table 7.

EXAMPLES

Isolating BAC 123H04M

A BAC ("bacterial artificial chromosome") which corresponded to the candidate region which had previously been located on chromosome 1, was isolated in order to identify a gene encoding a novel FMO. A library of BACs covering the complete human genome was prepared from the DNA of a human lymphoblast cell line which was derived from individual No. 8445 of the CEPH families. This cell line was used as the source of high molecular weight DNA. The DNA was partially digested with the restriction enzyme BamH1 and then cloned into the BamH1 site of the plasmid pBeloBacII. The resulting clones were pooled and screened using a three-dimensional analytical procedure which had previously been described for screening libraries of YACs ("yeast artificial chromosome") (Chumakov et al., 1992). The three-dimensional pools which were obtained were screened by PCR using primers which flanked the D1S3423 (WI-10286) marker. This STS ("sequence tagged site") had previously been located in the candidate region. One clone, of BAC 123H04M, was thus isolated.

Following digestion with the restriction enzyme NotI, the size of the insert carried by this BAC was determined in an 0.8% agarose gel after electrophoretic migration in an alternating field (CHEF) (4 hours at 9 volts/cm, with an angle of 100°, at 11° C. in 0.5×TAE buffer). This demonstrated that BAC 123H04M carries an insert of 180 kb.

Determining the Chromosomal Location of BAC 123H04M by Fluorescent in-situ Hybridization (FISH)

The chromosomal location of the BAC in the candidate region 1q23-q25 was confirmed by carrying out fluorescent in-situ hybridization (FISH) on metaphase chromosomes using the method described by Cherif et al., 1990. More precisely, BAC 123H04M was found to be located in band 1q23 of chromosome 1.

Sequencing the BAC 123H04M Insert

In order to sequence the BAC 123H04M insert, three separate libraries of subclones were prepared from the sonicated DNA of this BAC.

After incubation overnight, the cells derived from three liters of culture were treated by alkaline lysis in accordance with standard techniques. After centrifuging the resulting product on a cesium chloride gradient, 52 $\mu$g of the BAC 123H04M DNA were purified. 7 $\mu$g of DNA were sonicated under three different conditions in order to obtain fragments whose sizes were distributed uniformly over the range 1 to 9 kb. The resulting fragments were treated, in a volume of 50 $\mu$l, with 2 units of Vent polymerase at 70° C. for 20 minutes in the presence of the 4 deoxytriphosphates (100 $\mu$M). The blunt-ended fragments which resulted from this step were separated by electrophoresis in a 1% low melting point agarose gel (60 volts for 3 hours). The fragments, which were grouped according to their sizes, were excised and the bands which were obtained were treated with agarase. After extraction with chloroform and dialysis on microconcentrators trademarked as Microcon 100 columns, the dissolved DNA was adjusted to a concentration of 100 ng/$\mu$l. A ligation, involving overnight incubation, was performed by bringing 100 ng of the fragmented BAC 123H04M DNA into contact with 20 ng of the vector DNA, which had been linearized by enzymic digestion and treated with alkaline phosphatase. This reaction was carried out in a final volume of 10 $\mu$l and in the presence of 40 units of T4 DNA ligase (Epicentre)/$\mu$l. The ligation products were then used to transform, by electroporation, either an XL-Blue strain (for multicopy plasmids) or a D10HB strain (for the subclones derived from the BAC). The clones which were lacZ⁻ and resistant to the antibiotic were repicked individually into microplates for storage and sequencing.

This resulted in:

864 subclones derived from the insertion of fragments of from 2 to 3 kb in size into the SmaI site of plasmid puc18;

1728 subclones corresponding to the insertion of fragments of from 1.5 to 2 kb in size into the BamHI site (rendered blunt) of the plasmid trademarked as BluescriptSK;

288 subclones carrying fragments of from 4 to 7 kb in size which were inserted into the PmlI site of a modified BAC vector.

The inserts of these subclones were amplified by PCR, which was carried out on bacterial cultures which were incubated overnight and which used the vector primers which flanked the insertions. The sequences of the ends of these inserts (on average 500 bases at each end) were determined by automated fluorescent sequencing on an ABI 377 sequencer which was equipped with the ABI prism DNA Sequencing Analysis package (version 2.1.2).

The sequence fragments derived from the subBACs were assembled using R. Staden's Gap4 package (Bonfield et al., 1995). This package enables a complete sequence to be reconstructed from sequence fragments. The sequence deduced from aligning the different fragments is the consensus sequence.

Finally, directed sequencing techniques (systematic primer progression) were used to perfect the sequences and link the contigs.

Analysis of the Sequences

The potential exons of BAC 123H04M were pinpointed by carrying out homology searches on the public protein, nucleic acid and EST (expressed sequence tags) databases.

Databases

Use was made of local revisions of the main public databases. The protein database employed consists of the non-redundant fusion of the Genpept (automated GenBank™ translation, NCBI; Benson et al., 1996); Swissprot (George et al., 1996); and PIR/NBRF (Bairoch et al., 1996) databases. The duplicates were eliminated using the "nrdb" package (public domain, NCBI; Benson et al., 1996). The internal repetitions were then masked with the "xnu" package (public domain, NCBI; Benson et al., 1996). The resulting database, designated NRPU (non-redundant protein unique) was used as a reference for the protein homology searches. The homologies which were found with this database made it possible to locate regions which potentially encoded a protein fragment which was at least related to a known protein (coding exons). The EST database employed is composed of "gbest" subsections (1–9) of Genbank (NCBI; Benson et al., 1996). It contains all the public transcript fragments.

The homologies which were found using this database made it possible to locate potentially transcribed regions (present on the messenger RNA).

The database of nucleic acids (other than the ESTs) which was employed contains all the other subsections of Genbank and EMBL (Rodriguez-Tome et al., 1996), the duplicates of which were eliminated as described above.

Packages

Use was made of all the BLAST package (public domain, Altschul et al., 1990) for searching for homologies between a sequence and protein or nucleic acid databases. The significance thresholds depend on the length and complexity of the region tested as well as the size of the reference database. They were adjusted and adapted for each analysis.

Identification of FMO-Associated Genetic Polymorphisms in Relation to a Phenotypic Polymorphism which is Associated with the Occurrence of Juvenile Glaucoma, J-POAG, which is a Disease which is Transmitted in an Autosomal Dominant Manner (Locus GLC1A)

Detection of polymorphisms/mutations

1) Extracting the DNA

The DNA is extracted from the peripheral venous blood following cell lysis, protein digestion, organic partition and, finally, precipitation with alcohol.

The blood (20 ml) is drawn, by peripheral venous puncture, into a tube containing EDTA.

It is diluted with an equal volume of double distilled water. After 10 minutes, the cells are collected by centrifuging at 1600 g for 10 minutes. This manipulation is repeated.

The white cells are lysed in the presence of 20 ml of CLB buffer (10 mM Tris, pH 7.6, 5 mM $MgCl_2$, 0.32 M sucrose, 1% (v/v) Triton X-100). The nuclei are collected by centrifuging at 1600 g for 10 minutes. This manipulation is repeated.

The nuclei are washed once in RSB buffer (10 mM Tris, pH8, 10 mM NaCl, 10 mM EDTA). The pellet is resuspended in 2 ml of RSB buffer to which sodium lauryl sulfate (1%) and proteinase K (200 mg/ml) are added. The mixture is incubated at 55° C. for at least 3 hours and shaken regularly.

The resulting DNA solution is then extracted with one volume of phenol which is equilibrated with a 50 mM Tris, pH 8, buffer. This operation is repeated and finished off with an extraction with one volume of chloroform/isoamyl alcohol (24:1 v/v).

The DNA is precipitated with one volume of isopropanol, rinsed with ethanol (70%), dried and finally resuspended in 1 ml of TE buffer (10 mM Tris, pH 8, 0.5 mM EDTA). The concentration of DNA is determined by measuring the absorbance at 260 nm and taking 50 µg/ml of DNA as being equivalent to one absorbance unit. The DNA concentration is then adjusted to 200 µg/ml.

2) Amplification of the Genomic DNA

The oligonucleotide primers employed for the genomic amplification of the BAC 123H04M-derived exon sequences, as predicted by computer analysis, were defined using the OSP package (Hillier et al., 1991).

All these primers contain, upstream of the bases which are specifically targeted by the amplification, a common oligonucleotide tail which is intended to enable the amplified fragments to be sequenced (PU for the upstream primers and RP for the downstream primers; sequences shown in Table 5).

The oligonucleotide primers were synthesized on a GENSET UFPS 24.1 synthesizer using the phosphoramidite method.

Each predicted exon sequence was amplified by polymerase chain amplification reaction (PCR) under the following conditions:

| | |
|---|---|
| Final volume | 50 µl |
| Genomic DNA | 100 ng |
| MgCl2 | 2 mM |
| (for each) dNTP | 200 µM |
| (for each) primer | 7.5 pmol |
| AmpliTaq Gold DNA polymerase (Perkin) | 1 unit |
| * PCR buffer | 1 × |

* : (10 ×= 0.1 M Tris HCl, pH 8.3, 0.5 M KCl)

The amplification is performed in a Perkin Elmer 9600 or MJ Research PTC200 thermocycler with a heating lid. After heating at 94° C. for 10 minutes, 35 cycles are carried out. Each cycle comprises: 30 seconds at 94° C., 1 minute at 55° C. and 30 seconds at 72° C. A final segment of elongation at 72° C. for 7 minutes terminates the amplification.

The quantity of amplification products obtained is determined by fluorometry on a 96-well microplate using the intercalating agent Picogreen (molecular probes).

3) Detecting Polymorphisms/Mutations

Sequencing

The products of the PCR genomic amplification were sequenced on an automated ABI 377 sequencer using fluorescent primers, which were labeled with the ABI fluorochromes (Joe, Fam, Rox and Tamra), and Thermosequanase DNA polymerase (Amersham).

The reactions were performed in 96-well microplates on a Perkin Elmer 9600 thermocycler under standard temperature cycle conditions:

8 cycles: denaturation: 5 sec. at 94° C.; hybridization: 10 sec. ; elongation: 30 sec. at 72° C., then 13 cycles: denaturation: 5 sec. at 94° C.; elonga-tion: 30 sec. at 72° C.

6 units of Thermosequanase and 5–25 ng of amplification product were used per sequencing reaction.

Once the amplification cycles have been completed, the sequencing reaction products are precipitated in ethanol, resuspended in a loading buffer containing formamide, denatured and deposited on 4% acrylamide gels; the electrophoreses (2 hours 30 min at 3000 volts) are conducted on ABI 377 sequencers which are equipped with ABI collection and analysis software (ABI Prism DNA Sequencing Analysis Software, version 2.1.2.).

Analyzing the sequences

Since J-POAG is an autosomal dominant disease, the sequence data obtained were analyzed in order to detect the presence of heterozygosity sites in the patients suffering from juvenile glaucoma. The heterozygosity sites were confirmed after comparing the sequences of the two strands of genomic DNA from each individual concerned. A heterozygosity site is selected as a candidate mutation responsible for the occurrence of FMO-linked disorders when it is present in a population of members of one and the same family while being generally absent from the controls who are not related to the family.

Results

Out of all the BAC 123H04M-derived amplification fragments studied, one exhibits a heterozygosity site which segregates with the occurrence of juvenile glaucoma in a pedigree depicted in FIG. 1.

This heterozygosity site (G/A) is present in 7 patients suffering from J-POAG whereas it is absent from 3 healthy homozygous patients (GIG), with all the patients being derived from the same family. Furthermore, 99 unrelated controls are similarly homozygous (G/G) for this site, indicating that the frequency of the A allele in the general population is less than 0.005.

The site is contained in exon 8 of the gene which encodes the hFMO2 protein according to the invention; the described mutation transforms glutamic acid in position 402 of the sequence SEQ ID No. 1 of hFMO2 into lysine.

It is surprising to note that calculating the lod scores which integrate the preceding data for different assumptions of the frequency of each allele in the general population indicates a probability of greater than 100 to 1 that the described heterozygosity (G/A) is linked to J-POAG (Table 6). This probability is significant due to the fact that the analysis related to one single family.

The primers which enabled the DNA fragment containing this heterozygosity site to be amplified are described in Table 1.

TABLE 1

Sequences of the primers employed for amplifying the exon region which was derived from BAC 123H04M and which contains a heterozygosity site which is linked to juvenile POAG Locus of the fragment FMO2/Exon 8
Size of the amplified 420
fragment
Primers
Upstream PU (SEQ ID    5'TCACATAGAGTGCTATGGGGG
No.7)
Downstream RP (SEQ ID 5'CTTAGGAAGAAGATAAAAATGCAAC
No.8)

TABLE 2

Examples of primers for detecting the G.1263mac.A mutation by "Single Nucleotide Primer Extension"

a) SEQ ID No. 9    5'AATGTCCATCATCATAGTTCTCT 3'
                   (antisense)
   and/or
b) SEQ ID No. 10   5'TAGGCTTGTGTAGCCTGCCCTCA 3'
                   (sense)

TABLE 3

Identification of the G.1263mac.A mutation by RFLP

5' CCCTCAGAGAA 3'  "normal"

DdeI site (C TNAG)

5' CCCTCAaAGAAA 3' "mutant"

No cleavage

TABLE 4

Example of probes for detecting the G.1263mac.A. mutation by the ASO technique

Specific for the G allele

SEQ ID No. 11: 5' CCTCAGAAGAGAACTAT 3' and its complementary strand:

SEQ ID No. 12: 3' GGAGTCTCTCTTGATA  5'

Specific for the A allele

SEQ ID No. 13: 5' CCTCAAAGAGAACTAT  3' and its complementary strand:

SEQ ID No. 14: 3' GGAGTTTCTCTTGATA  5'

TABLE 5

Sequences of the primers employed for sequencing the amplification fragments derived from the genomic DNA

| Pu | 5' TGTAAAACGACGGCCAGT |
|----|----------------------|
| RP | 5' CAGGAAACAGCTATGACC |

TABLE 6

Lod score between the G.1263mac.A polymorphism and the juvenile POAG in the studied family as a function of the frequency of the two alleles in the general population

| Frequency of the rare (A) allele | Θ (recombination rate) | Lod score |
|---|---|---|
| 0.01 | 0 | 2.07 |
| 0.001 | 0 | 2.10 |
| 0.0001 | 0 | 2.10 |
| 0.00001 | 0 | 2.10 |

TABLE 7A

| FMO2 | Position in the gene (SEQ ID NO: 1) | Position in the mRNA (SEQ ID NO: 2) |
|---|---|---|
| Exon 1 | 2001–2056 | 1–56 |
| Exon 2 | 2405–2542 | 57–194 |
| Exon 3 | 10026–10214 | 195–383 |
| Exon 4 | 13341–13503 | 384–546 |
| Exon 5 | 16036–16178 | 547–689 |
| Exon 6 | 20558–20757 | 690–889 |
| Exon 7 | 21972–22327 | 890–1245 |
| Exon 8 | 24411–24483 | 1246–1318 |
| Exon 9 | 25487–25899 | 1319–1731 |
| ATG | 2411–2413 | 63–65 |
| Stop | 25836–25838 | 1668–1670 |

TABLE 7B

| FMOx | Position in the gene (SEQ ID NO: 4) | Position in the mRNA (SEQ ID NO: 5) |
|---|---|---|
| Exon 1 | 2001–2138 | 1–138 |
| Exon 2 | 6961–7149 | 139–327 |
| Exon 3 | 10144–10306 | 328–490 |
| Exon 4 | 11413–11555 | 491–633 |
| Exon 5 | 13347–13546 | 634–833 |
| Exon 6 | 15697–16052 | 834–1189 |
| Exon 7 | 17930–18002 | 1190–1262 |

TABLE 7B-continued

| FMOx | Position in the gene (SEQ ID NO: 4) | Position in the mRNA (SEQ ID NO: 5) |
|---|---|---|
| Exon 8 | 24838–25180 | 1263–1605 |
| CDS | 2006–25180 | 6–1605 |

TABLE 8

FMO2 Homology Between Macaque and Human

| | Length (numcleotide) | % Amino Acid Homology | % DNA Homology |
|---|---|---|---|
| Exon 1 (5' UTR) | 64 | — | 95.3 |
| Exon 2 | 137 | 100 | 96.5 |
| Exon 3 | 188 | 98 | 96.8 |
| Exon 4 | 162 | 96.7 | 96.9 |
| Exon 5 | 142 | 95.8 | 96.5 |
| Exon 6 | 199 | 95.4 | 97 |
| Exon 7 | 355 | 98.3 | 97.7 |
| Exon 8 | 72 | 96 | 97.2 |
| Exon 9 (3' UTR) | 413 | 93 | 95 |
| Total | | 96 | 96.7 |

TABLE 9

Variations Between Human and Macaque FMO2

| Position in Macaque mRNA | Macaque Nucleotide | Human Nucleotide | Amino acid |
|---|---|---|---|
| 56 | A | G | Non-Coding |
| 71 | A | G | – |
| 83 | C | T | – |
| 104 | G | A | – |
| 197 | G | T | Lys –> Asn |
| 218 | C | T | – |
| 266 | T | C | – |
| 284 | C | T | – |
| 344 | C | T | – |
| 360 | T | C | – |
| 404 | G | A | – |
| 455 | T | C | – |
| 482 | T | C | – |
| 499 | C | G | Ser –> Thr |
| 510 | T | A | Ile –> Phe |
| 548 | C | G | Ile –> Met |
| 604 | T | C | Ser –> Phe |
| 629 | C | T | – |
| 650 | C | A | – |
| 676 | G | A | Asn –> Ser |
| 725 | T | C | – |
| 729 | G | A | Val –> Ala |
| 743 | T | C | Arg –> Gln |
| 758 | G | A | – |
| 811 | T | C | – |
| 844 | A | G | – |
| 995 | T | C | – |
| 1085 | T | C | Glu –> Asp |
| 1121 | G | A | Phe –> Leu |
| 1133 | A | C | – |
| 1145 | G | C | – |
| 1155 | T | C | Ser –> His |
| 1157 | T | C | Ser –> His |
| 1160 | A | G | – |
| 1251 | C | A | – |
| 1252 | A | G | Tyr –> Phe |
| 1370 | T | C | – |
| 1448 | G | C | – |
| 1450 | T | A | – |
| 1473 | C | N | – |
| 1484 | A | G | – |

TABLE 9-continued

Variations Between Human and Macaque FMO2

| Position in Macaque mRNA | Macaque Nucleotide | Human Nucleotide | Amino acid |
|---|---|---|---|
| 1486 | C | T | – |
| 1509 | G | N | – |
| 1510 | C | N | – |
| 1514 | G | A | – |
| 1516 | G | A | – |
| 1535 | A | G | – |
| 1541 | G | A | – |
| 1556 | A | C | – |
| 1567 | T | C | – |
| 1590 | C | T | – |
| 1598 | C | T | – |
| 1623 | G | C | – |
| 1646 | C | T | – |
| 1677 | T | C | – |
| 1678 | G | A | – |

REFERENCES

The following publications are incorporated herein by reference in their entireties:

Allen J. B., Walberg M. W., Edwards M. C. & Elledge S. J. Finding prospective partners in the library: the two hybrid system and phage display find a match. TIBS 20: 511–516 (1995).

Altschul, Stephen F., Gish W., Miller W., Myers E. W., & Lipman D. J. Basic local alignment search tool. J. Mol. Biol. 215:403–10 (1990).

Bairoch A. & Apweiler R. The SWISS-PROT protein sequence data bank and its new supplement TREMBL. Nucleic Acids Res. 24: 21–25 (1996).

Belmouden A., Adam M. F., Dupont de Dinechin S., Brézin A. P., Rigault P., Chumakov I., Bach J-F., & Garchon H-J., 1996, Recombinational and physical mapping of the locus for primary open-angle glaucoma (GLC1A) on chromosome 1q23–q25. Genomics, sous presse.

Benson D. A., Boguski M., Lipman D. J. & Ostell J. GenBank. Nucleic Acids Res. 24: 1–5 (1996).

Bonfield J. K., Smith K. F. & Staden R. A new DNA sequence assembly program. Nucleic Acids Res. 23: 4992–9 (1995).

Buckholz R. G. Yeast Systems for the Expression of Heterologous Gene Products. Curr. Op. Biotechnology 4: 538–542 (1993).

Cashman J. R., Park, B. P., Berkman, C. E. & Cashman, L. E. Rôle of hepatic flavin-monoxygenase 3 in drug and chemical metabolism in adult humans. Chemico-Biological Interactions 96:33–46 (1995).

Carter B. J. Adeno-Associated virus vectors. Curr. Op. Biotechnology 3: 533–539 (1993).

Cherif D., Julier C., Delattre O., Derré J. Lathrop G. M., & Berger R.: Simultaneous localization of cosmids and chromosome R-banding by fluorescence microscopy—Applications to regional mapping of chromosome 11. Proc.Natl.Acad.Sci. USA. 87: 6639–6643 (1990).

Chumakov I., Rigault P., Guillou S., Ougen P., Billault A., Guasconi G., Gervy P., Le Gall I., Soularue P., Grinas P. et al. Continuum of overlapping clones spanning the entire human chromosome 21q. Nature 359: 380–386 (1992).

Chumakov I. M., Rignault P., Le Gall I. et al. A YAC contig map of the human genome. Nature 377 supplt: 175–183 (1995).

Compton J. Nucleic Acid Sequence-Based Amplification. Nature 350: 91–92 (1991).

Danos O., Moullier P. & Heard J. M. Réimplantation de cellules génétiquement modifiées dans des néo-organes vascularisés (Reimplantation of genetically modified cells in vascularized neoorgans). Médecine/Sciences 9:62–64 (1993).

Edwards C. P. et Aruffo A. Current applications of COS cell based transient expression systems. Curr. Op. Biotechnology 4: 558–563 (1993).

Epstein A. : Les vecteurs herpetiques pour le transfert de gènes (Herpesvirus vectors for transferring genes)- Médecine/Sciences 8: 902–911 (1992).

George D. G., Barker W. C.,. Mewes H. W, Pfeiffer F. & Tsugita A. The PIR-International Protein Sequence Database. Nucleic Acids Res. 24: 17–20 (1996).

Guatelli J. C. et al. Isothermal in vitro amplification of nucleic acids by a multienzyme reaction modeled after retroviral replication. Proc. Natl. Acad. Sci. USA 87: 1874–1878 (1990).

Hillier L. & Green P. OSP: a computer program for choosing PCR and DNA sequencing primers. PCR Methods Appl. 1: 124–8 (1991).

Hines et al., Toxicol. Appl. Pharmacol. 125, 1–6 (1994).

Landegren U., Kaiser R., Sanders J. & Hood L. A ligase-mediated gene detection technique. Science 241: 1077–1080 (1988).

Lawton M. P., Cashman J. R., Cresteil T., Dolphin C. T., Elfarra A. A., Hines R. N., Hodgson E., Kimura T., Ozols J., Phillips I. R., Philpot R. M., Poulsen L. L., Rettie A. E., Shephard E. A., Williams D. E., & Ziegler D. M.: A nomenclature for the mammalian flavin-containing monooxygenase gene family based on amino acid sequence identities. Arch. Biochem. Biophys. 308:1, 254–257 (1994).

Luban J. & Goff S. P. The yeast two-hybrid system for studying protein—protein interactions. Current Op. Biotechnology 1995, 6:59–64.

Luckow V. A. Baculovirus systems for the expression of human gene products. Curr. Op. Biotechnology 4: 564–572 (1993).

Olins P. O. et Lee S. C. Recent advances in heterologous gene expression in *E. coli*. Curr. Op. Biotechnology 4:520–525 (1993).

Park, S. B. et al., Chem. Res. Toxicol. 5, 193–201 (1992).

Perricaudet M., Stratford-Perricaudet L., & Briand P. : La thérapie génique par adénovirus (Gene therapy using adenoviruses)—La Recherche 23: 471–473 (1992).

Poulsen, L. L. et al., Chem. Biol. Interact. 96, 57–73 (1995).

Rodriguez-Tome P., Stoehr P. J., Cameron G. N., & Flores T. P. The European Bioinformatics Institute (EBI) databases. Nucleic Acids Res. 24: 6–12 (1996).

Samiotaki M., Kwiatkowksi M. Parik J., & Landegren U. Dual-color detection of DNA sequence variants through ligase-mediated analysis. Genomics 20: 238–242 (1994).

Schwartzman, M. L., Masferrer, J., Dunn M. W., McGiff J. C., Abracham N. G., 1987, Curr Eye Res. 6 : 623–630.

Schwartzman M. L., Balazy M., Masferrer J., Abraham, N. G., McGiff, J. C., Murphy, R. C., 1987, PNAS USA 84 : 8125–8129.

Stoneking M., Hedgecock D., Higuchi R. G., Vigilant L., & Erlich H. A. Population variation of human DNA control region sequences by enzymatic amplification and sequence-specific oligonucleotide probes. Am. J. Hum. Genet. 48: 370–382 (1991).

Sunden S. L. F., Alward W. L. M., Nichols B. E., Rokhlina T. R., Nystuen A., Stone E. M. & Sheffield V. C. Fine mapping of the autosomal dominant juvenile open angle glaucoma (GLC1A) region and evaluation of candidate genes. Genome research 6: 862–869 (1996).

Syvänen A. C., Aalto-Setala K., Harju L., Kontula K., & Soderlund H. A primer-guided nucleotide incorporation assay in the genotyping of Apo E. Genomics 8: 684–692 (1990).

Temin H. M.: Retrovirus vectors for gene transfer. In Kucherlapati R., ed. Gene Transfer, New York, Plenum Press, 149–187 (1986).

Walker G. T., Fraiser M. S., Schram J. L., Little M. C., Nadeau J. G., & Malinowski D. P. Strand displacement amplification: an isothermal in vitro DNA amplification technique. Nucleic Acids Res. 20: 1691–1696 (1992).

Wu D. Y., Ugozzoli L. Pal B. K., Wallace R. B. Allele-specific amplification of b-globin genomic DNA for diagnosis of sickle cell anemia. Proc. Natl. Acad. Sci. USA 86: 2757–2760 (1989).

Ziegler, D. M., , Drug Metab. Rev. 19, 1–32 (1988).

Ziegler, D. M., Annu. Rev. Pharmacol. Toxicol., 33, 179–199 (1993).

---

What is claimed is:

1. A composition comprising an isolated and purified polypeptide comprising the amino acid sequence of SEQ ID NO: 3 having Flavin Monooxygenase activity.

2. The composition of claim 1, wherein said polypeptide is a recombinant polypeptide.

3. A method of screening for inhibitors of the polypeptide of claim 1 comprising the steps of:
   a) contacting said polypeptide with a test substance; and
   b) measuring Flavin Monooxygenase activity of said polypeptide; wherein a decrease in said activity indicates that the test compound is an inhibitor of said polypeptide.

4. A method of producing the polypeptide of claim 1 comprising the steps of:
   a) culturing a host cell capable of expressing the polypeptide of claim 1 under conditions suitable for producing said polypeptide; and
   b) isolating and purifying said polypeptide produced by the cell.

5. A composition comprising an isolated and purified polypeptide fragment of SEQ ID NO:3 comprising amino acids 45–107.

6. The composition of claim 5, wherein said polypeptide is a recombinant polypeptide.

7. A method of producing the polypeptide of claim 5 comprising the steps of:
   a) culturing a host cell capable of expressing the polypeptide of claim 5 under conditions suitable for producing said polypeptide; and
   b) isolating and purifying said polypeptide produced by the cell.

8. A composition comprising an isolated and purified polypeptide fragment of SEQ ID NO:3 comprising amino acids 108–535.

9. The composition of claim 8, wherein said polypeptide is a recombinant polypeptide.

10. A method of producing the polypeptide of claim 8 comprising the steps of:
   a) culturing a host cell capable of expressing the polypeptide of claim 8 under conditions suitable for producing said polypeptide; and
   b) isolating and purifying said polypeptide produced by the cell.

* * * * *

UNITED STATES PATENT AND TRADEMARK OFFICE
CERTIFICATE OF CORRECTION

PATENT NO.    : 6,551,792 B1
DATED         : April 22, 2003
INVENTOR(S)   : Marta Blumenfeld et al.

It is certified that error appears in the above-identified patent and that said Letters Patent is hereby corrected as shown below:

Column 12,
Line 36, "MRNA" should read -- mRNA --.

Column 21,
Line 10, "(GIG)," should read -- (G/G), --.

Column 22,
Line 8, Table 4, "SEQ ID NO. 11 : 5' CCTCA G̅ AAGAGAACTAT 3'" should read

-- SEQ ID NO. 11 : 5' CCTCA G̅ AGAGAACTAT 3' --.

Signed and Sealed this

Twenty-third Day of September, 2003

JAMES E. ROGAN
*Director of the United States Patent and Trademark Office*